(12) United States Patent
Takahashi

(10) Patent No.: US 11,160,479 B2
(45) Date of Patent: Nov. 2, 2021

(54) INFORMATION PROCESSING DEVICE AND CONTROL METHOD

(71) Applicant: SONY CORPORATION, Tokyo (JP)

(72) Inventor: Ryo Takahashi, Tokyo (JP)

(73) Assignee: SONY CORPORATION, Tokyo (JP)

( * ) Notice: Subject to any disclaimer, the term of this patent is extended or adjusted under 35 U.S.C. 154(b) by 641 days.

(21) Appl. No.: 15/560,230

(22) PCT Filed: Jan. 21, 2016

(86) PCT No.: PCT/JP2016/051735
§ 371 (c)(1),
(2) Date: Sep. 21, 2017

(87) PCT Pub. No.: WO2016/170810
PCT Pub. Date: Oct. 27, 2016

(65) Prior Publication Data
US 2018/0184959 A1    Jul. 5, 2018

(30) Foreign Application Priority Data
Apr. 23, 2015    (JP) .............................. JP2015-088170

(51) Int. Cl.
*A61B 5/16*    (2006.01)
*A61B 5/00*    (2006.01)
(Continued)

(52) U.S. Cl.
CPC ............ *A61B 5/165* (2013.01); *A61B 5/0022* (2013.01); *A61B 5/01* (2013.01); *A61B 5/0205* (2013.01);
(Continued)

(58) Field of Classification Search
CPC ... A61B 5/165; G06F 3/011; G06F 2203/011; G06N 3/006; G06K 9/00671
See application file for complete search history.

(56) References Cited

U.S. PATENT DOCUMENTS 10,133,918 B1 * 11/2018 Chang ................ G06K 9/00362
2010/0145695 A1 * 6/2010 Jung ....................... G10L 17/26
704/246
(Continued)

FOREIGN PATENT DOCUMENTS

JP        2010-094493 A    4/2010
JP        2013-029928 A    2/2013
(Continued)

OTHER PUBLICATIONS

Hancock et al. (2008). I'm sad you're sad: Emotional contagion in CMC. Proceedings of the ACM conference on Computer-Supported Cooperative Work (CSCW 2008). (Year: 2008).*
(Continued)

*Primary Examiner* — Meredith Weare
(74) *Attorney, Agent, or Firm* — Chip Law Group

(57) ABSTRACT

An information processing device including an emotion recognition unit that recognizes, on the basis of information concerning a user and information concerning another user having been sensed, an emotion of the other user, and a notification control unit that performs control such that the user is notified of information concerning the emotion of the other user having been recognized.

15 Claims, 19 Drawing Sheets

(51) Int. Cl.
*A61B 5/01* (2006.01)
*H04M 1/72436* (2021.01)
*A61B 5/0205* (2006.01)
*A61B 5/11* (2006.01)
*A61B 5/1171* (2016.01)
*G06Q 10/10* (2012.01)

(52) U.S. Cl.
CPC ........... *A61B 5/1118* (2013.01); *A61B 5/1176* (2013.01); *A61B 5/4803* (2013.01); *A61B 5/6802* (2013.01); *A61B 5/7405* (2013.01); *A61B 5/7445* (2013.01); *H04M 1/72436* (2021.01); *A61B 5/163* (2017.08); *G06Q 10/1093* (2013.01); *H04M 2250/12* (2013.01)

(56) References Cited

U.S. PATENT DOCUMENTS

| | | | | |
|---|---|---|---|---|
| 2012/0072939 | A1* | 3/2012 | Crenshaw | H04N 21/4415 725/12 |
| 2013/0095460 | A1* | 4/2013 | Bishop | G09B 19/00 434/308 |
| 2014/0118225 | A1* | 5/2014 | Jerauld | A61B 5/7278 345/8 |
| 2015/0061824 | A1 | 3/2015 | Suzuki et al. | |
| 2015/0118663 | A1* | 4/2015 | Levy | G09B 5/02 434/236 |

FOREIGN PATENT DOCUMENTS

| | | |
|---|---|---|
| JP | 2013-052049 A | 3/2013 |
| JP | 2013-239914 A | 11/2013 |
| JP | 2015-046070 A | 3/2015 |

OTHER PUBLICATIONS

Mauss et al. "Measures of emotion: A review." Cogn Emot. Feb. 1, 2009; 23(2): 209-237. (Year: 2009).*

International Search Report and Written Opinion of PCT Application No. PCT/JP2016/051735, dated Apr. 26, 2016, 9 pages of ISRWO.

Hancock et al., "I'm sad you're sad: Emotional Contagion in CMC", Computer Supported Cooperative Work, ACM, 2 Penn Plaza, Suite 701 New York 10121-0701 USA, XP058175861, Nov. 8, 2008, 4 pages.

Office Action for EP Patent Application No. 16782832.6, dated Mar. 3, 2021, 7 pages of Office Action.

* cited by examiner

FIG. 8

FORECAST OF MOOD OF MS. A ON JANUARY 7

| TIME | 00:00-06:00 | 06:00-12:00 | 12:00-18:00 | 18:00-24:00 |
|---|---|---|---|---|
| MOOD | ORDINARY | GOOD | VERY BAD | VERY GOOD |
| EMOTION | NORMAL | HAPPY | TENSE | CHEERFUL |
| OBSERVED EXPRESSION | (face) | (face) | NOT YET ACQUIRED | NOT YET ACQUIRED |
| RELIABILITY | 20% | 40% | 80% | 60% |
| FACTOR HAVING INFLUENCED FORECAST | • PLEASANT SLEEP | • LUNCH MENU OF THE DAY IS FAVORITE ONE | • CONDUCT PRESENTATION IN FRONT OF SUPERIORS IN AFTERNOON | • EATING OUT WITH COLLEAGUES FOR CELEBRATION |

FIG. 9

FORECAST OF MOOD OF MS. A IN SECOND WEEK OF JANUARY

| DATE | JAN 5 (MON) | JAN 6 (TUE) | JAN 7 (WED) | JAN 8 (THU) | JAN 9 (FRI) | JAN 10 (SAT) | JAN 11 (SUN) |
|---|---|---|---|---|---|---|---|
| MOOD | VERY BAD | ORDINARY | SLIGHTLY BAD | BAD | GOOD | VERY GOOD | ORDINARY |
| EMOTION | OPPRESSED | NORMAL | TENSE | SAD | HAPPY | SATISFIED | DEPRESSED |
| OBSERVED EXPRESSION | | | | NOT YET ACQUIRED | NOT YET ACQUIRED | NOT YET ACQUIRED | NOT YET ACQUIRED |
| RELIABILITY | 80% | 20% | 60% | 50% | 30% | 80% | 40% |
| FACTOR HAVING INFLUENCED FORECAST | • HEAVY PERIOD DAY | • NO PLAN EXCEPT WORK | • CONDUCT PRESENTATION IN FRONT OF SUPERIORS IN AFTERNOON | • SECOND ANNIVERSARY OF GRANDMOTHER'S DEATH | • DRINKING PARTY IS GOING TO BE HELD AT NIGHT | • HOT SPRING TRIP WITH BOY FRIEND | • MEETING IS GOING TO BE HELD FIRST IN MORNING NEXT DAY |

FIG. 11

| HOST: | MR. AAA |
|---|---|
| SUBJECT: | DECISION ON POLICY REGARDING BBB |
| PLACE: | CCC MEETING ROOM |
| START DATE AND TIME: | JAN 7 (WED) 10:30 |
| COMPLETION DATE AND TIME: | JAN 7 (WED) 11:30 |

ATTENDEE:

| MR. DDD, GENERAL MANAGER | MR. EEE, SECTION MANAGER | MR. FFF, SECTION CHIEF | MR. GGG |
|---|---|---|---|
| 2.0 | 4.0 | 1.0 | 3.0 |

PRODUCTIVITY CONTRIBUTION RATIO

OVERALL PRODUCTIVITY EVALUATION: B

[HOLD] [SUSPEND] [TIME CHANGE]

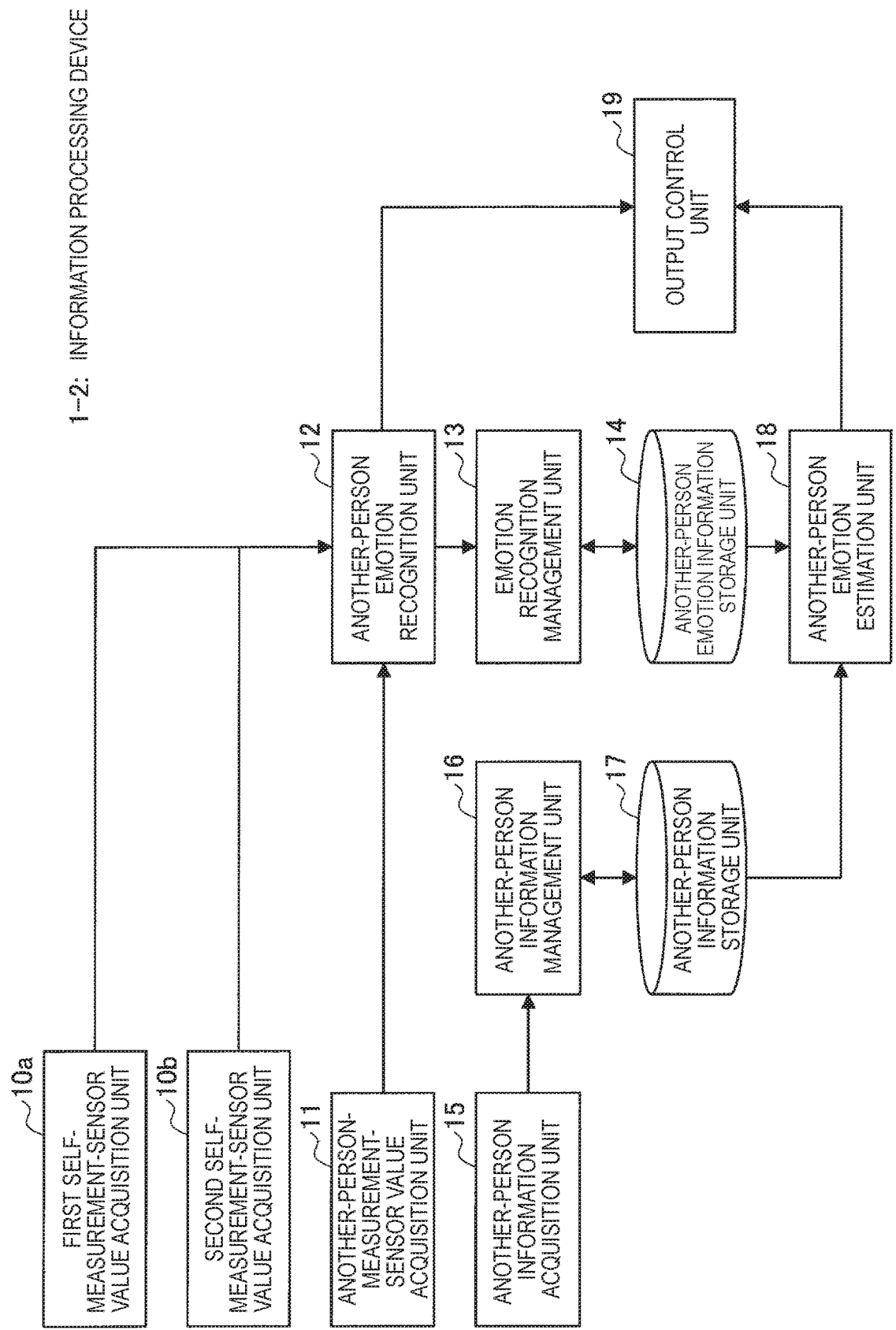

INFORMATION PROCESSING DEVICE AND CONTROL METHOD

CROSS REFERENCE TO RELATED APPLICATIONS

This application is a U.S. National Phase of International Patent Application No. PCT/JP2016/051735 filed on Jan. 21, 2016, which claims priority benefit of Japanese Patent Application No. JP 2015-088170 filed in the Japan Patent Office on Apr. 23, 2015. Each of the above-referenced applications is hereby incorporated herein by reference in its entirety.

TECHNICAL FIELD

The present disclosure relates to an information processing device, a control method, and a program.

BACKGROUND ART

In recent years, a technology for estimating a human emotion (psychological state) on the basis of biological information and controlling a device in accordance with the estimated biological information has been proposed.

For example, Patent Literature 1 below proposes an imaging device that sets a capturing parameter reflecting the psychological state of a person to be a subject and performs imaging.

CITATION LIST

Patent Literature

Patent Literature 1: JP2013-239914A

DISCLOSURE OF INVENTION

Technical Problem

The technology described in the Patent Literature 1 above detects the psychological state of a subject on the basis of the pulse rate, amount of sweating, and respiratory rate measured by a sensor device worn by the subject, the eye movement and blinking of the subject analyzed from a captured image captured by an imaging device held by a photographer, and the like.

However, such a technology forces another person who is a subject to wear a sensor device when performing imaging, and thus a problem arises in that usability is poor and it is not practical.

Therefore, the present disclosure proposes an information processing device, a control method, and a program that can recognize an emotion of another user using sensing information of a user.

Solution to Problem

According to the present disclosure, there is proposed an information processing device including: an emotion recognition unit configured to recognize, on the basis of information concerning a user and information concerning another user having been sensed, an emotion of the other user; and a notification control unit configured to perform control such that the user is notified of information concerning the emotion of the other user having been recognized.

According to the present disclosure, there is proposed a control method including: recognizing, on the basis of information concerning a user and information concerning another user having been sensed, an emotion of the other user; and performing control by a notification control unit such that the user is notified of information concerning the emotion of the other user having been recognized.

According to the present disclosure, there is proposed a program for causing a computer to function as: an emotion recognition unit configured to recognize, on the basis of information concerning a user and information concerning another user having been sensed, an emotion of the other user; and a notification control unit configured to perform control such that the user is notified of information concerning the emotion of the other user having been recognized.

Advantageous Effects of Invention

According to the present disclosure as described above, it is possible to recognize an emotion of another user using sensing information of a user.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 8 is a diagram showing an example of display of another-person emotions of a mood forecasting type according to the present embodiment.

FIG. 9 is a diagram showing another example of display of another-person emotions of the mood forecasting type according to the present embodiment.

FIG. 11 is a diagram showing a display screen example in a case where a result of estimating another-person emotions according to the present embodiment is output from a schedule management application.

FIG. 13 is a block diagram showing an example of a configuration of an information processing device according to a second embodiment.

MODE(S) FOR CARRYING OUT THE INVENTION

Figure 1:
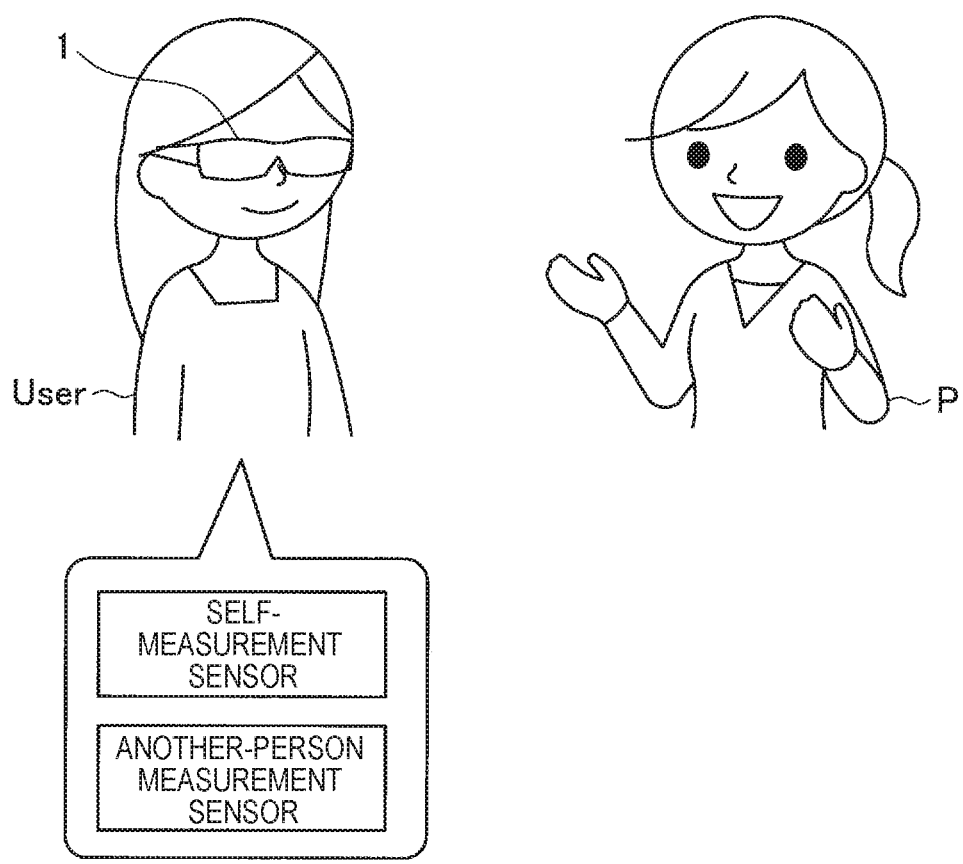
FIG. 1 is a diagram illustrating an overview of an information processing system according to an embodiment of the present disclosure.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

In addition, description will be provided in the following order.
1. Overview of an information processing system according to an embodiment of the present disclosure
2. Respective embodiments
2-1. First embodiment
2-1-1. Configuration
2-1-2. Operation
2-2. Second embodiment
2-3. Third embodiment
2-4. Fourth embodiment
2-5. Fifth embodiment
3. Hardware configuration of an information processing device 1
4. Conclusion

1. Overview of an Information Processing System According to an Embodiment of the Present Disclosure An information processing system according to an embodiment of the present disclosure is capable of recognizing an emotion of another person on the basis of a sensor value sensed from a user interacting with the other person.

In order to recognize an emotion (psychological state) of another person, it is conventionally required to have the other person wear a sensor device and analyze a captured image obtained by capturing an image of the other person. However, it is not practical to force the other person to wear a sensor device in order to become aware of an emotion of the other person. Moreover, it is not accurate as there are cases where the other person intentionally changes the facial expression in order to falsify his/her emotion.

Here, while interacting with another person, it is assumed that an emotion of the user is influenced by an emotion of the other person. For example, an emotion of the user while conducting a conversation with the other person face-to-face and an emotion of the other person are highly correlated, and their emotions often match in such a manner that in a case where the user feels joy, the other person also feels joy.

Therefore, the information processing system according to the present disclosure recognizes an emotion of the user on the basis of biological information sensed from the user or the like, and recognizes an emotion that matches, resembles, or correlates with that emotion as an emotion of another person (partner) interacting with the user. Accordingly, when recognizing an emotion of the other person who is an interaction partner using the present system, the user himself/herself only needs to wear (or hold) a predetermined sensor device, and it is not necessary to force the other person to wear a sensor device. Thus, it is practical and convenience is improved. Hereinafter, an overview of such an information processing system according to the present disclosure will be described with reference to FIG. 1.

FIG. 1 is a diagram illustrating an overview of an information processing system according to an embodiment of the present disclosure. As shown in FIG. 1, while a user and another person P are conducting a face-to-face conversation, an information processing device 1 worn by the user recognizes an emotion of the other person P on the basis of biological information or the like of the user sensed by a self-measurement sensor and a captured image or the like of the other person P sensed by an another-person measurement sensor. The information processing device 1 is implemented by a transparent glass-type terminal (SmartEyeglass) as shown in FIG. 1, for example, and notifies the user of the recognized emotion of the other person P by display on a lens portion or audio output. This allows the user to become aware of the emotion of the other person P in real time while being accompanied by the other person P without forcing the other person P to wear a sensor device.

Moreover, if an another-person emotion is recognized only on the basis of the expression of the other person P using a captured image of the other person P, it is not accurate as there are cases where the other person intentionally changes the facial expression in order to falsify his/her emotion as described above. In the present embodiment, however, an emotion of the other person P can be recognized more accurately because biological information or the like of the user under the influence of the other person P is also utilized.

Furthermore, at least part of the self-measurement sensor and the another-person measurement sensor may be mounted on the information processing device 1 worn by the user or may be mounted on another wearable device worn by the user (such as SmartBand, SmartWatch, or neck worn device, for example). Alternatively, at least part of the self-measurement sensor and the another-person measurement sensor may be mounted on a mobile terminal held by the user (such as mobile phone, smartphone, or tablet terminal, for example).

The above-described information processing system according to the present disclosure will be specifically described below using a plurality of embodiments.

2. Respective Embodiments

2-1. First Embodiment

First, a first embodiment of the present disclosure will be specifically described with reference to FIG. 2 to FIG. 11.
(2-1-1. Configuration)

Figure 2:
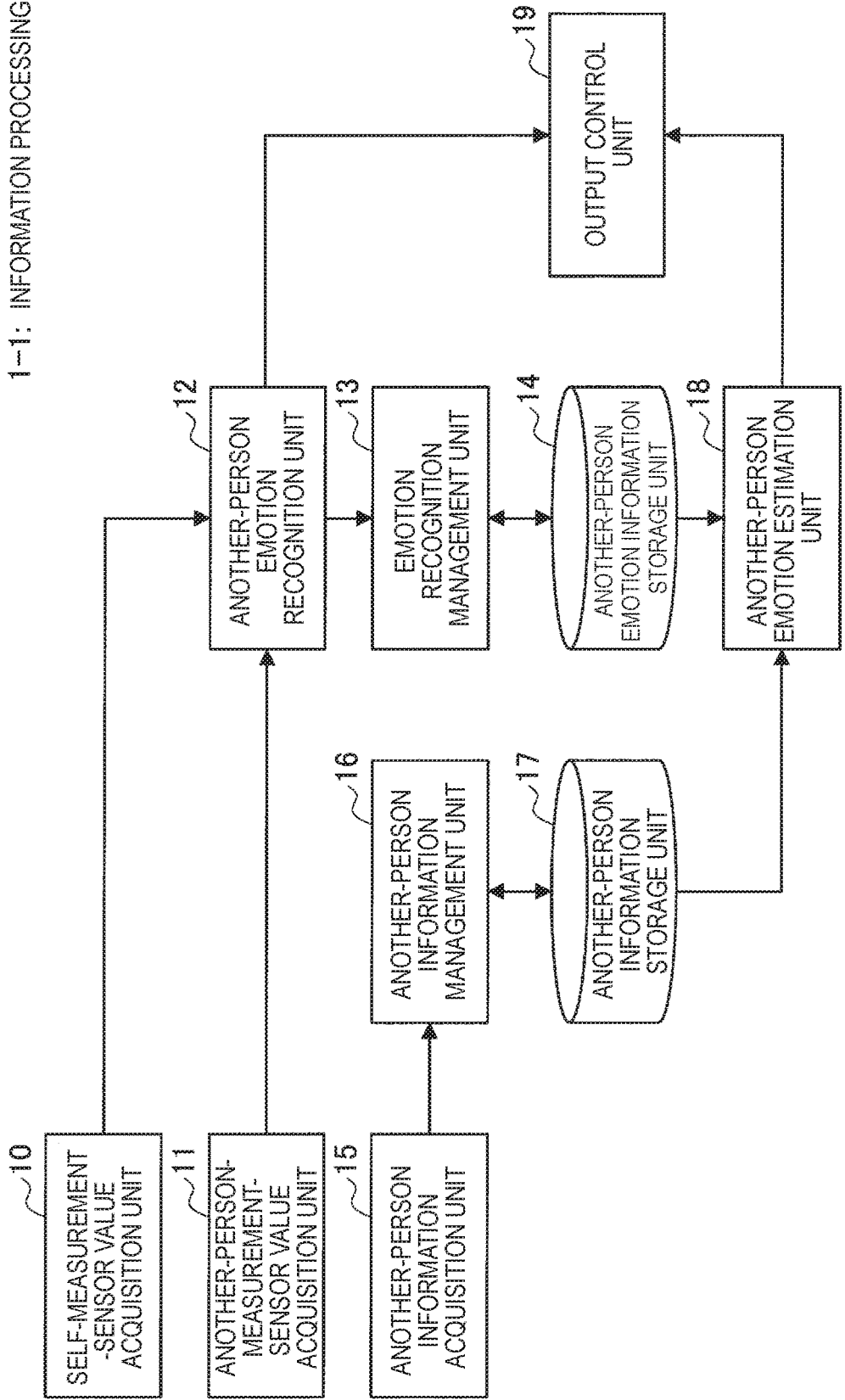
FIG. 2 is a block diagram showing an example of a configuration of an information processing device according to a first embodiment.

FIG. 2 is a block diagram showing an example of a configuration of an information processing device 1-1 according to the first embodiment. As shown in FIG. 2, the information processing device 1-1 has a self-measurement-sensor value acquisition unit 10, an another-person-measurement-sensor value acquisition unit 11, an another-person emotion recognition unit 12, an emotion recognition management unit 13, an another-person emotion information storage unit 14, an another-person information acquisition unit 15, an another-person information management unit 16, an another-person information storage unit 17, an another-person emotion estimation unit 18, and an output control unit 19.

The self-measurement-sensor value acquisition unit 10 acquires a sensor value sensed by a self-measurement sensor worn or held by a user. The self-measurement sensor may be implemented by a biosensor that senses biological information, such as a heart rate record, such as a pulse wave meter or electrocardiograph, a respiratory rate meter, a sweat sensor, a ballistocardiography, a thermometer, a blood pressure monitor, a blood glucose meter, a line-of-sight detection device, or a pupil measuring device, for example. Alternatively, the self-measurement sensor may be implemented by an amount-of-activity sensor that senses amount-of-activity information, such as an acceleration sensor, an angular velocity sensor, a pedometer, or a geomagnetic sensor, for example. Alternatively, the self-measurement sensor may be implemented as their combination.

Various types of self-measurement sensors may be mounted on a wearable device worn by the user (such as the information processing device 1 implemented by SmartEyeglass, SmartBand, SmartWatch, or neck worn device, for example), or may be mounted on a mobile terminal of the user. In a case where the self-measurement sensor exists as an external device of the information processing device 1, the self-measurement-sensor value acquisition unit 10 receives a sensor value from the external self-measurement sensor through wireless or wired communication.

The another-person-measurement-sensor value acquisition unit 11 acquires a sensor value sensed by the another-person measurement sensor that senses another person. The another-person measurement sensor may be implemented by a camera, microphone, depth indicator, proximity sensor, human presence sensor, thermography, or the like, for example, or may be implemented as their combination. Alternatively, the another-person measurement sensor may be mounted on a wearable device worn by the user, or may be mounted on a mobile terminal held by the user. In addition, the another-person measurement sensor is also capable of sensing an accompanying third party from the viewpoint that an emotion of the other person also influences an emotion of the third party.

In the present specification, another person refers to a subject of emotion recognition according to the present system, and a partner interacting with the user by a conversation or the like (a directly facing partner or a partner not directly facing but interacting over the telephone or the like). In addition, a third party refers to a person other than a partner who is a subject of emotion recognition, and is a person interacting with the user and the other person by a conversation or the like.

Figure 3:
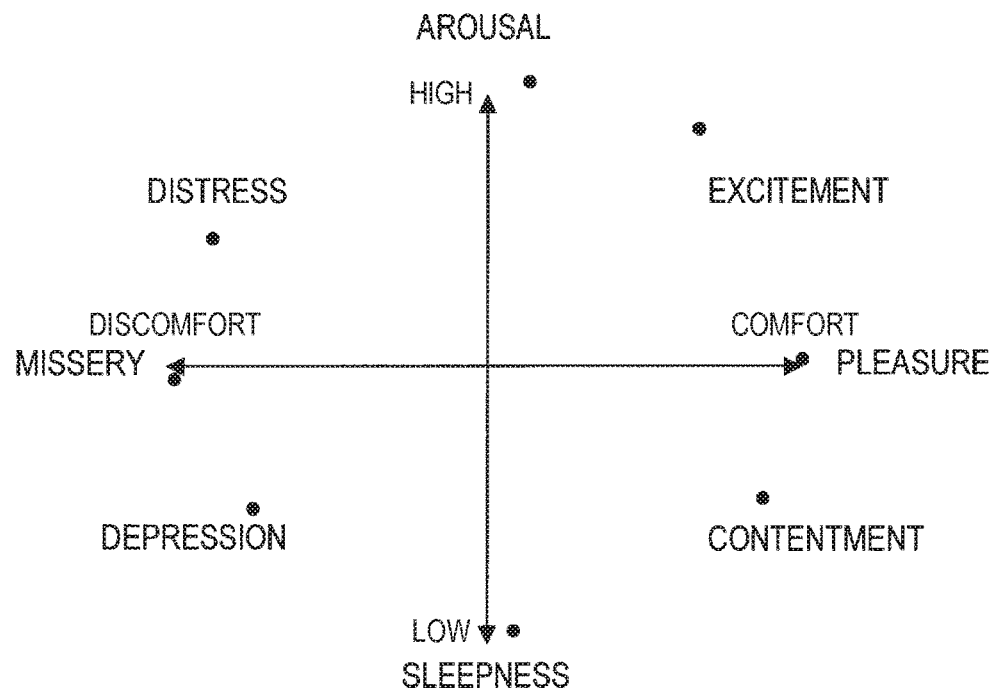
FIG. 3 is a diagram showing a two-dimensional circumplex model of emotions.

The another-person emotion recognition unit 12 recognizes an emotion of the other person on the basis of a self-measurement sensor value acquired by the self-measurement-sensor value acquisition unit 10 and an another-person measurement sensor value acquired by the another-person-measurement-sensor value acquisition unit 11. The another-person measurement sensor value acquired by the another-person-measurement-sensor value acquisition unit 11 may be a sensor value obtained by sensing a third party from the viewpoint that an emotion of the other person also influences an emotion of the third party as described above, besides a sensor value related to the other person. Moreover, various methods of classifying human emotions have been proposed, and an emotion classifying method by Russell, for example, by means of a two-dimensional circumplex model is used in the present embodiment. FIG. 3 is a diagram showing a two-dimensional circumplex model of emotions. The two-dimensional circumplex model shown in FIG. 3 covers emotions as a whole by arranging the respective emotions on the ring on two-dimensional axes of the degree of arousal level (arousal-sleepness) and the degree of comfort emotion (comfort-discomfort). Note that other examples include classification into six emotions of surprise, fear, anger, aversion, sadness, and happiness proposed by Paul Ekman, for example.

Figure 4:
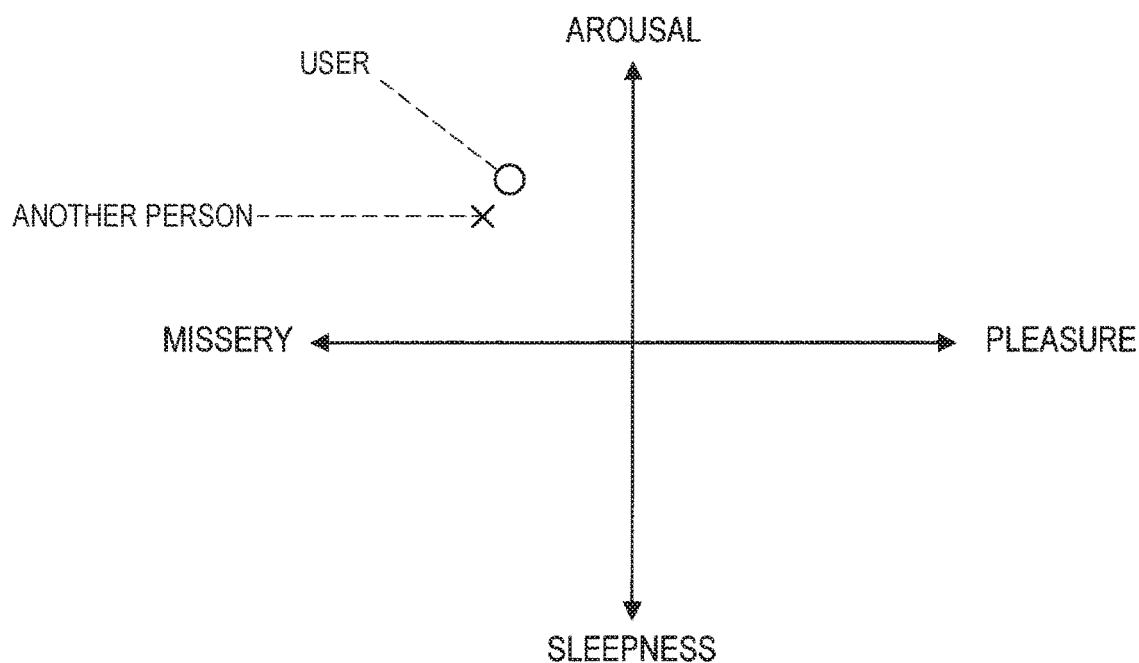
FIG. 4 is a diagram illustrating that a user and another person are similar in emotional mapping in the two-dimensional circumplex model.

Here, in many cases, the user is influenced by another person (partner) with whom the user is interacting, and an emotion of the user and an emotion of the other person often match, resemble, or correlate. That is, when mapping emotions of accompanying two persons on the two-dimensional circumplex model, the user and the other person are often similar in emotion mapping as shown in FIG. 4.

Therefore, the another-person emotion recognition unit 12 according to the present embodiment recognizes an emotion of the user on the basis of the respective sensor values, and recognizes an emotion that matches, resembles, or correlates with that emotion as an emotion of the other person. Note that correlated emotions also include an emotion against the emotion of the user.

More specifically, the another-person emotion recognition unit 12 is capable of recognizing an emotion of the other person using a machine learning technique, such as support vector machine (SVM), deep learning, or the like, and a statistical technique or the like on the basis of a feature quantity extracted from the self-measurement sensor value and a feature quantity extracted from the another-person sensor.

As a feature quantity extracted from the self-measurement sensor value, R-R interval, average value of intervals, root mean square, LF/HF ratio (ratio between low frequency (LF) and high frequency (HF)) or the like is extracted as a feature quantity in a case where the self-measurement sensor is a pulse wave meter, for example. Alternatively, in a case where the self-measurement sensor is a respiratory-rate measurement sensor, an average value, root mean square, or the like of the respiratory rate may be extracted as a feature quantity. Alternatively, in a case where the self-measurement sensor is a sweat sensor, a skin conductance level (SCL) or the like may be extracted as a feature quantity. Alternatively, in a case where the self-measurement sensor is an acceleration sensor, a peak value, average speed, or the like may be extracted as a feature quantity.

Moreover, as a feature quantity extracted from the another-person measurement sensor value, a gray value, gradient value, four directional features, HOG feature, Haar-like feature, or the like is extracted from a captured image (still image/video) as a feature quantity in a case where the another-person measurement sensor is a camera, for example. In addition, in a case where a face could have been detected from a captured image, expression-related information, such as the rise/fall degree of corners of a mouth, eyebrows, lips, or eyelids, opening/closing of a mouth or eyes, or the like may further be extracted as a feature quantity. In addition, in a case where a body could have been detected from the captured image, information concerning the posture or movement of the other person may be extracted as a feature quantity. In addition, in a case where the another-person measurement sensor is a thermography, temperature information of the other person may be extracted from an infrared image as a feature quantity. Alternatively, in a case where the another-person measurement sensor is a microphone, the fundamental frequency or sound pressure of voice of the other person, speech speed, first to third formants and their bandwidths, or the like may be extracted as a feature quantity.

The another-person emotion recognition unit 12 is capable of inputting feature quantities, such as an LF/HF ratio acquired from a pulse wave meter and SCL acquired from a sweat sensor particularly in connection with a self-measurement sensor value as well as the rise/fall degree of corners of a mouth or eyebrows acquired from a camera in connection with an another-person measurement sensor value to a recognition algorithm based on a machine learning technique to recognize an another-person emotion.

For the recognition algorithm used for an another-person emotion, four cases described below, for example, are considered. First, as a case 1, a recognition algorithm for general purpose independent of a user and a subject of emotion recognition (another person), that is, not specialized in an individual is assumed. Moreover, as a case 2, a recognition algorithm generated for each user, that is, specialized in an individual user is assumed. Furthermore, as a case 3, a recognition algorithm generated for each subject of emotion recognition (another person), that is, specialized in individual another person is assumed. Then, as a case 4, a recognition algorithm generated for each user and each subject of emotion recognition (another person), that is, specialized in a combination of a user and specific another person is assumed. The recognition algorithm in the above-described case 1 may be stored in advance in the information processing device 1-1, for example, and the recognition algorithms in the above-described case 2 to case 4 may be generated by the another-person emotion recognition unit 12.

The emotion recognition management unit 13 has a function of managing a result recognized by the another-person emotion recognition unit 12 in the another-person emotion information storage unit 14. Specifically, the emotion recognition management unit 13 stores a result recognized by the another-person emotion recognition unit 12 in the another-person emotion information storage unit 14. At this time, the emotion recognition management unit 13 may store another-person information highly correlated with an another-person emotion (action-related information, such as schedule information, physiological phenomenon information, or income and expenditure information) acquired by the another-person information acquisition unit 15 when recognizing the another-person emotion, in association with the another-person emotion.

The another-person emotion information storage unit 14 is a database that stores a result recognized by the another-person emotion recognition unit 12.

The another-person information acquisition unit 15 acquires various types of information related to another person from a predetermined server or the like on a network. For example, the another-person information acquisition unit 15 acquires various types of information related to another person through a service such as social networking service (SNS) or from a database located in a corporation or an educational institution. As specific examples of various types of information related to another person, physiological phenomenon-related (such as menstrual cycle, meal, excretion, manic-depression, or drug ingestion), schedule-related (such as association with friends/acquaintances, attendance at a meeting, delivery date, business trip, coming to/returning from work, coming to/returning from school, examination, or holidays), income and expenditure-related (such as remittance of salary/bonus, purchase history, or withdrawal from/deposit in a bank account), and others (such as winning/losing of a favorite sports team or stock price change) are assumed. Note that another-person information to be acquired may be restricted in accordance with the relationship between the user and the other person. Acquisition of another-person information related to a physiological phenomenon, for example, may be limited to a case where the user and the other person are family.

The another-person information management unit 16 has a function of managing another-person information acquired by the another-person information acquisition unit 15 in the another-person information storage unit 17. Specifically, the another-person information management unit 16 stores another-person information acquired by the another-person information acquisition unit 15 in the another-person information storage unit 17.

The another-person information storage unit 17 is a database that stores another-person information acquired by the another-person information acquisition unit 15.

The another-person emotion estimation unit 18 estimates a future emotion of the other person on the basis of past another-person emotion information (also referred to as an another-person emotion history) stored in the another-person emotion information storage unit 14 and another-person information (specifically, action-related information of another person) stored in the another-person information storage unit 17. For example, the another-person emotion estimation unit 18 performs trend estimation by a statistical technique or the like to estimate a future emotion of the other person from a situation indicated by the another-person information. Specifically, the another-person emotion estimation unit 18 is capable of performing such estimation that the mood generally tends to be bad in periods of "attendance at a meeting" and "delivery date" (tends to have a tense or depressive mood) and that the mood generally tends to be good in a period of "remittance of salary/bonus" (tends to have a happy or cheerful emotion) to estimate a future emotion of the other person. In addition, in a case where another-person emotions and another-person information have been accumulated in the another-person emotion information storage unit 14 in association with each other, the another-person emotion estimation unit 18 is also capable of estimating an emotion tendency specific to the other person using the past another-person emotion history to estimate an another-person emotion.

The output control unit 19 performs output control through an output device (not shown) so as to notify the user of the another-person emotion recognized by the another-person emotion recognition unit 12. A notification to the user may be a display notification or an audio notification. Moreover, the output control unit 19 can inform the user of a current emotion of another person (partner) currently accompanying the user by performing control such that the user is notified in real time of the another-person emotion recognized by the another-person emotion recognition unit 12. Furthermore, the output control unit 19 may inform the user of a future another-person emotion estimated by the another-person emotion estimation unit 18. In a case where the information processing device 1-1 is implemented by SmartEyeglass, the output device (not shown) may be a transparent display device that corresponds to a lens portion located before the user's eyes while wearing, or may be a speaker located close to an ear of the user while wearing. The speaker can notify the user alone of an another-person emotion more reliably by implementing the speaker by a directional speaker or a bone-conductive speaker. In addition, the output control unit 19 is not limited to a display device or audio output device provided in the information processing device 1-1, but may transmit notification information to an external device, such as a display device or audio output device provided in a mobile terminal held by the user, for output through the external device.

Further, the output control unit 19 may display a notification of another-person emotions by graphical representation. Description will be provided below showing an example in FIG. 5.

Figure 5:
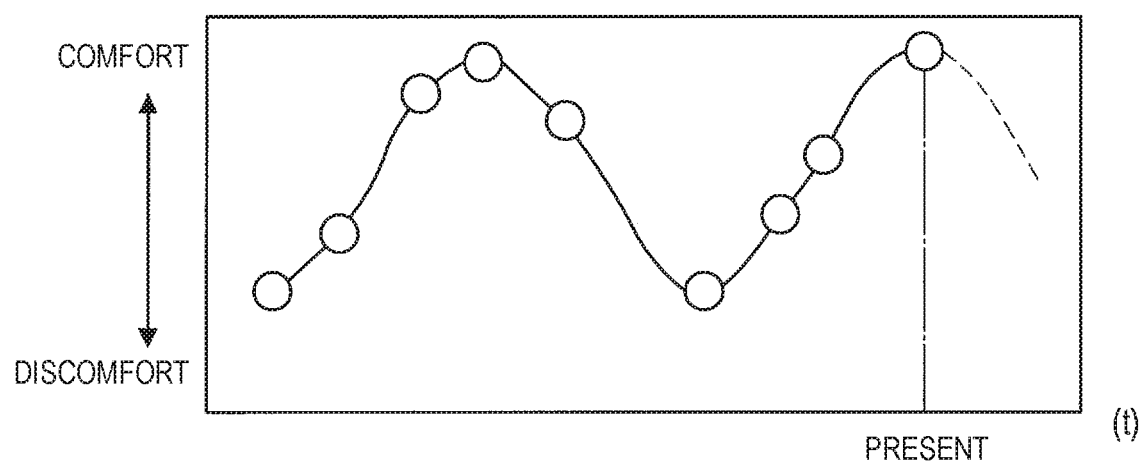
FIG. 5 is a diagram showing an example of a graph representing a transition of another-person emotions (comfort-discomfort) according to the present embodiment.

FIG. 5 is a diagram showing an example of a graph representing a transition of another-person emotions (comfort-discomfort) according to the present embodiment. In FIG. 5, a time-series transition of accumulated past another-person emotions, a recognized current another-person emotion, and an estimated future another-person emotion is represented graphically. The graph shown in FIG. 5 allows the user to intuitively grasp that the mood of another person (partner) is becoming better gradually and will then become bad.

The configuration of the information processing device 1-1 according to the present embodiment has been specifically described above. Note that the configuration of the information processing device 1-1 is not limited to the example shown in FIG. 2, but at least a part may be present on a network (so-called cloud), for example.

(2-1-2. Operation)

Figure 6:
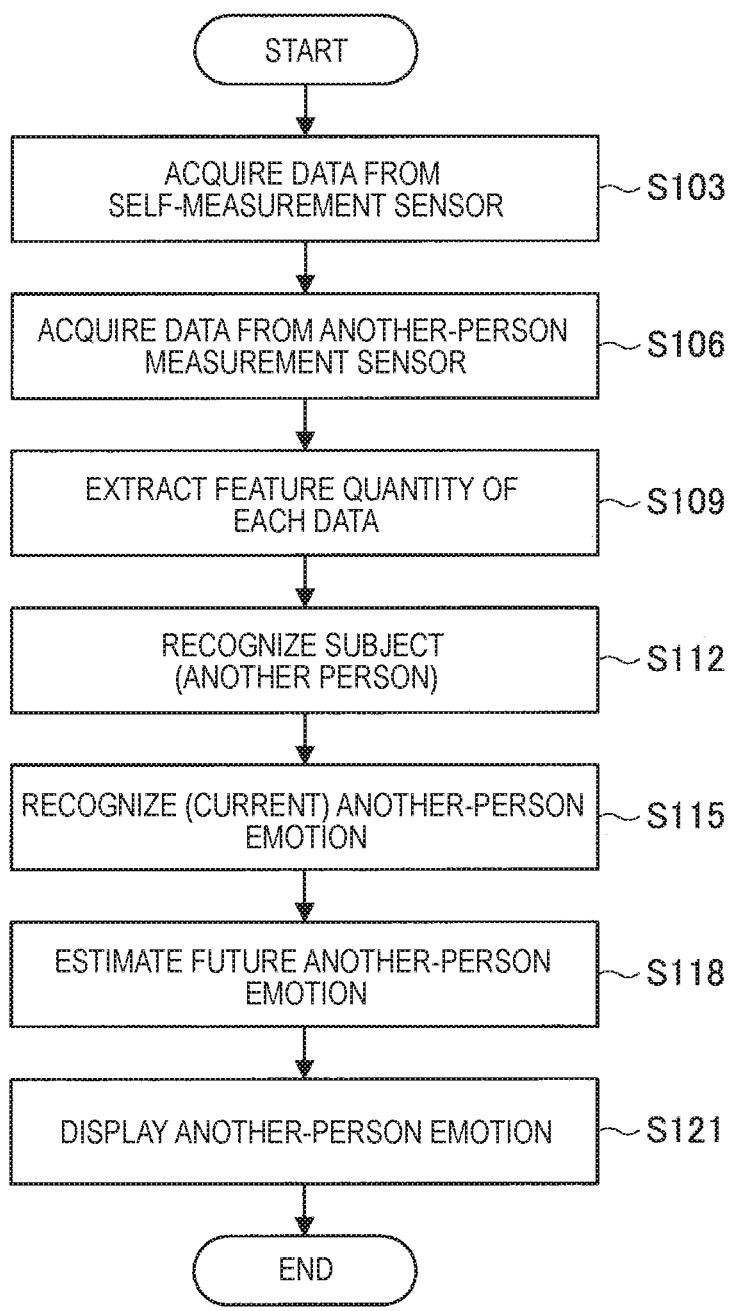
FIG. 6 is a flowchart showing an another-person emotion recognizing process according to the present embodiment.

Subsequently, an operational process according to the present embodiment will be described with reference to FIG. 6. FIG. 6 is a flowchart showing an another-person emotion recognizing process according to the present embodiment. As shown in FIG. 6, first, in step S103, the self-measurement-sensor value acquisition unit 10 of the information processing device 1-1 acquires sensing data of a user from the self-measurement sensor (also referred to as a self-measurement sensor value). At this time, the self-measurement-sensor value acquisition unit 10 subjects the acquired data to noise reduction and resampling, and formats the data into data easily utilized in processing in a later stage.

Next, in step S106, the another-person-measurement-sensor value acquisition unit 11 acquires sensing data of another person (also referred to as an another-person measurement sensor value) from the another-person measurement sensor. At this time, the another-person-measurement-sensor value acquisition unit 11 subjects the acquired data to noise reduction and resampling, and formats the data into data easily utilized in processing in a later stage. In addition, another person in the present embodiment is a partner interacting with the user, and is assumed to be a person conducting a face-to-face conversation with the user, for example.

Then, in step S109, the another-person emotion recognition unit 12 extracts a feature quantity of each data from the self-measurement sensor value and the another-person measurement sensor value. For example, the another-person emotion recognition unit 12 extracts a feature quantity such as an LF/HF ratio acquired from a heart rate sensor or SCL acquired from a sweat sensor in connection with the self-measurement sensor value and the corners of a mouth or eyebrows acquired from a camera in connection with the another-person measurement sensor.

Subsequently, in step S112, the another-person emotion recognition unit 12 performs recognition of a subject (another person) whose emotion is to be recognized. Specifically, the another-person emotion recognition unit 12 recognizes the other person facing the user on the basis of the feature quantity of the another-person measurement sensor value obtained from the another-person measurement sensor. The recognition of the other person may be discrimination between presence and absence of the other person (whether the user is accompanied by someone), or may be discrimination as to whether the other person is an acquaintance of the user. Discrimination between presence and absence of the other person is performed depending on whether a conversation is being conducted with the user on the basis of a result of conversation recognition, for example. Moreover, although the subject of another-person emotion recognition is not limited to an acquaintance of the user in the flow shown in FIG. 6, in a case of limiting another-person emotion recognition to an acquaintance of the user, the another-person emotion recognition unit 12 performs discrimination as to whether the other person is an acquaintance depending on whether the other person corresponds to a friend registered on SNS or corresponds to a person belonging to the same community, such as a corporation or educational institution, on the basis of a result of another-person face recognition, for example.

Next, in step S115, the another-person emotion recognition unit 12 recognizes a current another-person emotion. Specifically, the another-person emotion recognition unit 12 recognizes an emotion of the other person recognized in the above S112 using a machine learning technique, such as a neural network, on the basis of a feature quantity of the self-measurement sensor value and a feature quantity of the another-person measurement sensor value. For example, the another-person emotion recognition unit 12 maps the respective feature quantities in a feature space using the following expression 1 to recognize an emotion of the other person. In the following expression 1, the total number of feature quantities is denoted by N, and the respective feature quantities by $V_1, V_2 \ldots V_N$. In addition, the respective feature quantities may be subjected to predetermined weighting.

$$f(v_1, v_2 \ldots v_N) = \sum_{i=0}^{N} \omega_i v_N \qquad \text{(expression 1)}$$

Next, in step S118, the another-person emotion estimation unit 18 estimates a future emotion of the other person on the basis of the another-person emotion history and another-person information. For example, the another-person emotion estimation unit 18 applies the another-person emotion history to a statistical model, such as an autoregressive model, to estimate a future emotion of the other person. At this time, the another-person emotion estimation unit 18 is capable of referring to information highly correlated with an emotion, such as the menstrual cycle, from the another-person information stored in the another-person information storage unit 17 to increase accuracy in estimating an another-person emotion. In addition, the another-person emotion estimation unit 18 is also capable of regarding information such as winning/losing of a sports team which is a favorite with the other person as a stimulus to increase accuracy in estimating an another-person emotion.

Then, in step S121, the output control unit 19 performs control such that the recognized another-person emotion or estimated another-person emotion is displayed and the user is notified thereof. Moreover, when the output control unit 19 notifies the user of the recognized current another-person emotion in real time, the user can become aware of a current emotion of a partner currently in conversation in real time.

The another-person emotion recognizing process according to the present embodiment has been specifically described above. Note that the above-described process is an example, and the present embodiment is not limited to this. For example, the output control unit 19 may compare a current another-person emotion recognized by the another-person emotion recognition unit 12 and a future another-person emotion estimated by the another-person emotion estimation unit 18, and in a case where it is predicted that the mood of the other person will change remarkably from now on, may notify the user of the change in mood.

Furthermore, the output control unit 19 may compare an average mood based on the another-person emotion history and a future another-person emotion, and in a case where a statistically significant difference arises, may determine that the mood of the other person will be improved/worsened and notify the user of the change in mood. Alternatively, the output control unit 19 may determine the change in mood on the basis of a specific threshold standard without using a statistical technique.

(2-1-3. Display Example)

Subsequently, a display example of a notification to a user of another-person emotions by the output control unit 19 of the present embodiment will be specifically described with reference to FIG. 7 to FIG. 11.

Figure 7:
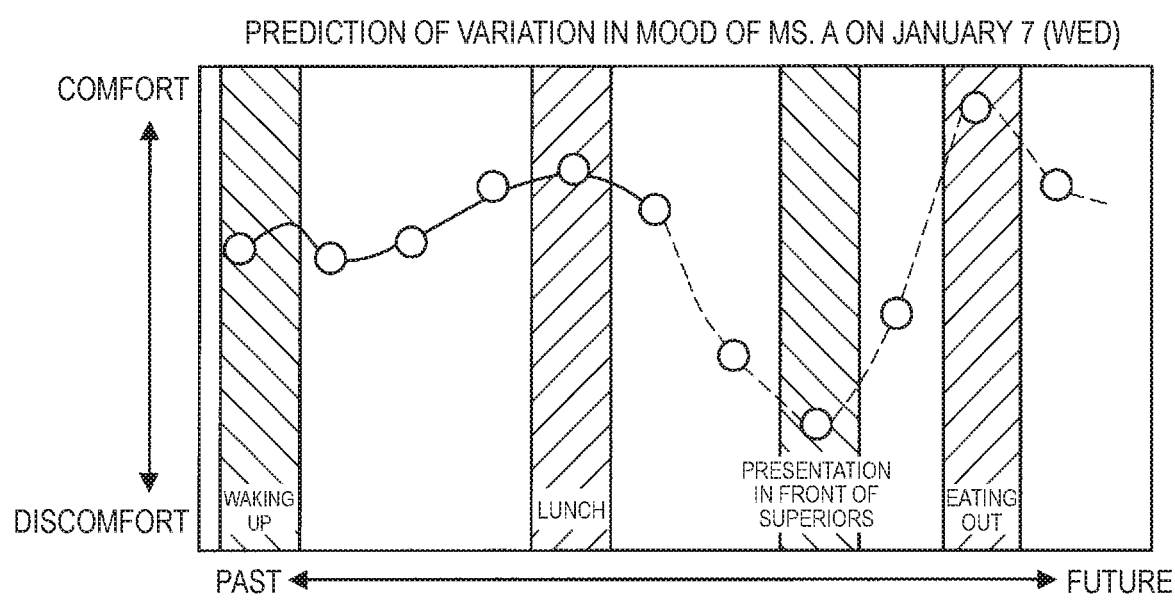
FIG. 7 is a diagram showing an example of a graphical display of another-person emotions along with another-person schedule information according to the present embodiment.

FIG. 7 is a diagram showing an example of a graphical display of another-person emotions along with another-person schedule information according to the present embodiment. The graph shown in FIG. 7 shows a transition of another-person emotions from the past to the future similarly to the graph shown in FIG. 5, and specifically, the solid line part shows past another-person emotions and the broken line part shows future another-person emotions. In addition, in the example shown in FIG. 7, events highly correlated with emotions are extracted from another-person information and displayed together with the graph. This allows the user to intuitively grasp that another person is in a good mood when having "lunch" and "eating out", and is in a bad mood when making a "presentation in front of superiors" (changed to a tense state or depressive state). Note that the degree of disclosure of the schedule of the other person to the user may be changed in accordance with the relationship between the user and the other person. In a case where the new density between the user and the other person is high (that is, the privacy level is low), for example, the output control unit 19 causes a displayed schedule to be displayed in a thinner manner and in a larger number (or causes a schedule that satisfies the degree of disclosure in accordance with the privacy level to be displayed).

FIG. 8 is a diagram showing an example of display of another-person emotions of a mood forecasting type according to the present embodiment. As shown in FIG. 8, in the mood forecast, emotions estimated by the another-person emotion estimation unit 18 on the basis of the another-person information (such as schedule information) and the another-person emotion history are displayed every several hours. This allows the user to grasp a transition of moods of another person in one day.

Specifically, in the mood forecast, the time, mood (very good-good-ordinary-bad-very bad), emotion (such as cheerful, happy, normal, tense), reliability, and a factor having influenced the forecast are displayed at each time. Note that the "mood" is determined in accordance with an emotion estimated by the another-person emotion estimation unit 18. Moreover, the "emotion" may be displayed by text, or may be displayed by a face image that expresses an emotion (such as an avatar, illustration, or an edited version of a real face image of the other person, for example) as shown in FIG. 8.

Furthermore, in a case where an emotion of the other person could have been actually observed after display of the mood forecast, the output control unit 19 may display a face image in accordance with the emotion of the other person actually observed as an "observed expression." In the example shown in FIG. 8, while it was forecast that an another-person emotion would be "normal" at 0:00-06:00, it is seen from the face image that an another-person emotion actually observed was also "normal." Moreover, while it was forecast that an another-person emotion would be "happy" at 06:00-12:00, it is seen from the face image that an another-person emotion actually observed was "normal." In addition, in a case where an actual another-person emotion could have not been observed or the time has not arrived yet, "not yet acquired" is displayed in the field of "observed expression."

Moreover, as shown in FIG. 8, forecast reliability may also be displayed in the mood forecast display. The forecast reliability is calculated on the basis of a population of the another-person emotion history utilized when the another-person emotion estimation unit 18 estimates an another-person emotion, presence/absence of an event (that is, a factor) highly correlated with an emotion included in the another-person information and the strength of correlation, forecasting accuracy up to now, and the like, for example.

Furthermore, as shown in FIG. 8, a factor having influenced the forecast may also be displayed in the mood forecast display. Such a factor is extracted from the another-person information, and is an event highly correlated with an emotion utilized for estimation of an another-person emotion, and, for example, the sleeping time, meal time, contents of meal (whether it is a favorite dish, etc.), work schedule (inside duty, outside duty, business trip, presentation, etc.), crowded level of train during commutation, or the like is assumed. Here, whether to display or hide a factor to be disclosed to the user may be decided in accordance with the relationship between the user and the other person.

The display example of another-person emotions of the mood forecasting type has been specifically described above. Note that a mood forecast display example in one day (every several hours) is shown in the example shown in FIG. 8, whilst the present embodiment is not limited to this, but a mood forecast display example in a week (on a daily basis) may be adopted as shown in FIG. 9, for example.

FIG. 9 is a diagram showing another example of display of another-person emotions of a mood forecasting type according to the present embodiment. As shown in FIG. 9, in the weekly mood forecast, a mood forecast of another person (Ms. A, for example) from Monday to Sunday is displayed. More detailed descriptions on displayed moods, emotions, observed expressions, reliability, and factors having influenced the forecast are similar to the example of mood forecast described with reference to FIG. 8.

Note that expressions showing emotions of the other person actually observed are displayed in the examples shown in FIG. 8 and FIG. 9, whilst the present embodiment is not limited to this, but the other person himself/herself may be allowed to give feedback. For example, a case where an actually observed expression and a true emotion of the other person are different is also assumed, and therefore, when the other person himself/herself gives feedback about his/her own emotions to the present system, a true another-person emotion is fed back to the user, and is utilized for improving another-person emotion estimation in accuracy, which improves convenience of the present system.

The graphs and mood forecast images described above may be displayed on a display unit of a user's smartphone, mobile phone, tablet terminal, personal computer (PC), or the like. In addition, in a case where the information processing device 1 is implemented by SmartEyeglass, the output control unit 19 may cause the graphs and mood forecast images described above to be displayed on a transparent display unit of the SmartEyeglass using an augmented reality (AR) technology. Description will be provided below with reference to FIG. 10.

Figure 10:
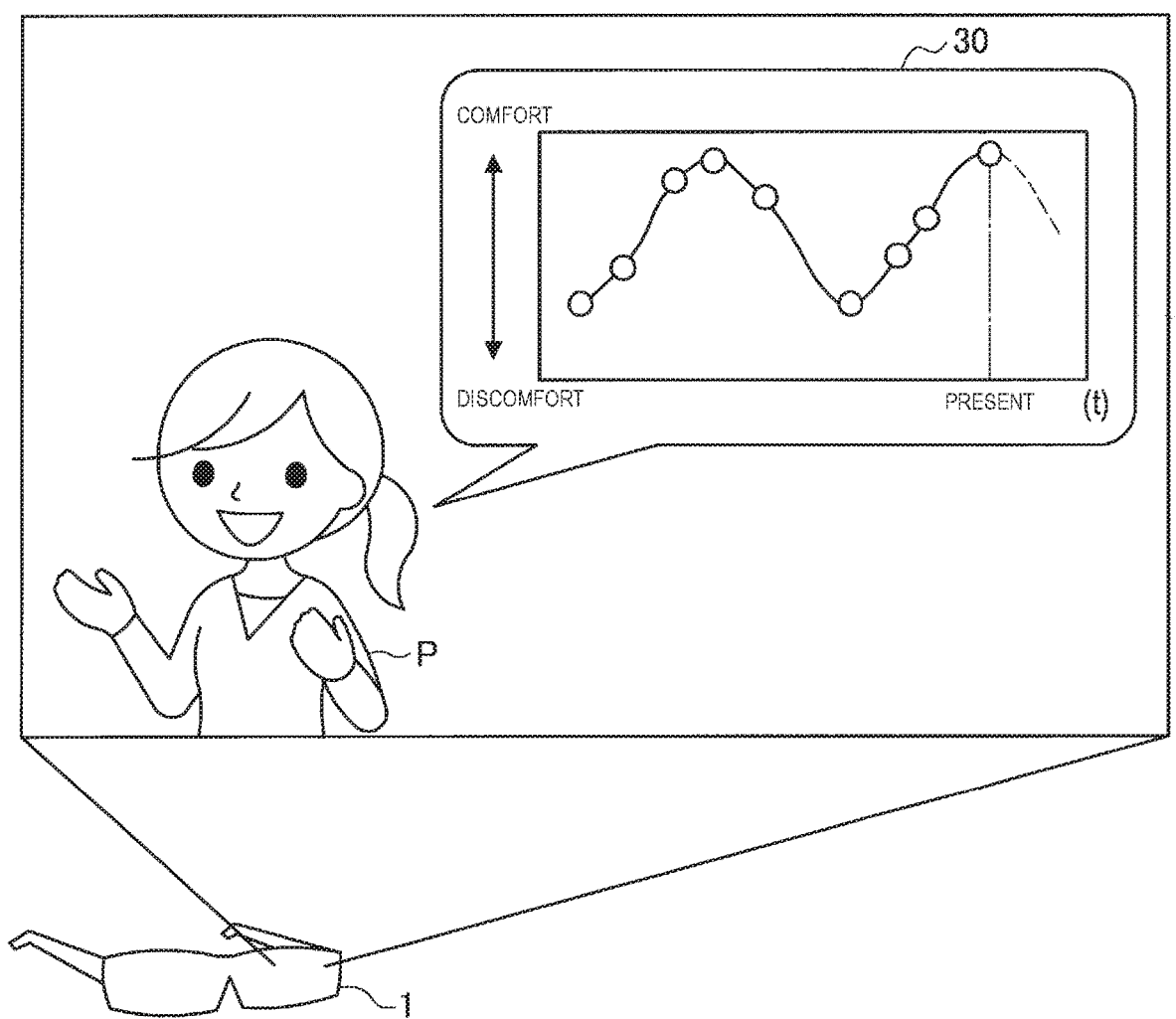
FIG. 10 is a diagram showing an example of a display notification of another-person emotions using an AR technology.

FIG. 10 is a diagram showing an example of a display notification of another-person emotions using the AR technology. When the information processing device 1 is implemented by SmartEyeglass as shown in FIG. 10, a transparent display unit is provided at a lens portion located before the user's eyes while being worn by the user. Here, while the user in a state wearing the information processing device 1 is conducting a conversation with another person, the information processing device 1 recognizes the other person present before the user's eyes to recognize and estimate an another-person emotion, and performs control such that a graph image 30 representing a transition of another-person emotions is displayed in a superimposed manner in real space in correspondence to the other person P present in real space, as shown in FIG. 10, for example. This allows the user to intuitively grasp an emotion of the conversation partner.

Note that the timing when display of an another-person emotion is performed may be when the information processing device 1 recognizes the other person P, or may be when it is determined that the user is giving attention to the other person P on the basis of the self-measurement sensor value (such as when detection of a user's line of sight is performed and it is determined that the user is looking at the other person P, for example).

Moreover, it is also possible to notify the user by voice of the graphs of a transition of another-person emotions and mood forecasts described above. For example, the output control unit 19 may make a forecast announcement such as "Ms. A will be in a good mood in the first half of the week, and sometimes in a bad mood in the latter half" through a speaker (not shown) provided in the information processing device 1.

Furthermore, the output control unit 19 according to the present embodiment may notify the user of a recognized/estimated another-person emotion in conjunction with another service or system. For example, the output control unit 19 is capable of displaying moods of attendees at a meeting in list form in conjunction with a corporate schedule management application. Description will be specifically provided below with reference to FIG. 11.

FIG. 11 is a diagram showing a display screen example in a case where a result of estimating another-person emotions according to the present embodiment is output from a schedule management application. As shown in FIG. 11, a schedule screen 32 includes schedule information such as host, subject, place, start date and time, completion date and time, and attendees. These pieces of information have been input by a user (here, "Mr. AAA") when making a schedule, for example.

Further, in the present embodiment, as shown in FIG. 11, a result of estimating an emotion of each attendee who participates in the meeting is displayed. Such a result of emotion estimation is obtained by estimating an emotion of each attendee on the date and time of the meeting by the another-person emotion estimation unit 18, and is represented by an expression of a character as shown in FIG. 11, for example. This allows a user to become aware that Mr. DDD, the general manager and Mr. FFF, the section chief seem to be in a bad mood during the meeting. In addition, not only an individual emotion of each attendee, but also an emotion as a group calculated by combining numeric values representing emotions of the respective attendees, for example, by a method such as a linear sum may be displayed on the schedule screen 32.

Additionally, in the present embodiment, a productivity contribution ratio of each attendee is also calculated in accordance with an estimated emotion of each attendee at the meeting, and is displayed in correspondence to a character representing an emotion of each attendee as shown in FIG. 11. Moreover, in the present embodiment, an evaluation of overall productivity as a group is also calculated on the basis of the estimated emotion and productivity contribution ratio of each attendee, and is displayed as "overall productivity evaluation" as shown in FIG. 11. The user can decide whether to hold, suspend, or time change the meeting with reference to these estimated emotions and productivity contribution ratios of the respective attendees and overall productivity evaluation.

Here, when the user selects a "time change" button included in the schedule screen 32, the information processing device 1 may look for a date and time at which the overall productivity evaluation is high from among predetermined days before and after the currently set date and time of the meeting on the basis of the results of estimation by the another-person emotion estimation unit 18 for proposal to the user.

In addition, in the present embodiment, the following use form may be considered as an example of utilizing a recognized/estimated another-person emotion in conjunction with another service or system. For example, in a case where the information processing device 1 is capable of controlling a music player, song selection is performed that reflects an emotion of another person, such as playing back an encouraging song when the other person accompanying the user is depressed, and a change in playback mode is made in accordance with an emotion of the other person by bringing an equalizer into a pops mode when the other person is relaxed. Accordingly, it is possible to entertain another person having visited the user's room by music, for example.

Moreover, in a case where the information processing device 1 is capable of controlling a camera, shutter control (such as clicking the shutter when the mood is good, for example), parameter setting, or switching of capturing mode (such as overexposing when the mood is good, for example) in accordance with an emotion of another person may be performed.

Furthermore, in a case where the information processing device 1 is capable of controlling a game machine, and when an emotion of another person having a game with the user is in a "bored" state, an attempt to highly maintain concentration of the other person on the game may be made by bringing about an event during the game or the like.

In addition, in a case where the information processing device 1 is capable of controlling illumination of a room, illumination control in accordance with an another-person emotion, such as changing illumination to a warm color temperature when another person is relaxed and enraptured, may be performed.

In this manner, the information processing device 1 according to the present embodiment can control music played in a room or illumination in accordance with a recognized/estimated emotion of another person without forcing the other person to wear a sensor device or the like to entertain the other person. Additionally, the information processing device 1 can perform appropriate camera control or game control in accordance with a recognized/estimated emotion of the other person.

As described above, the information processing system according to the present embodiment can recognize an emotion of another person using sensing information of the user without forcing the other person to wear a sensor device, and can implement a practical system. Moreover, the information processing system according to the present embodiment is also capable of estimating a future emotion of the other person on the basis of another-person information and an another-person emotion history to notify the user in advance, in addition to recognizing a current emotion of the other person in real time to immediately notify the user interacting with the other person.

Note that the information processing system according to the present embodiment may continuously recognize/estimate emotions of the other person not only when the user utilizes the present system voluntarily, and may notify the user when the mood of the other person seems to be improved/worsened significantly. The information processing system according to the first embodiment has been described above.

2-2. Second Embodiment

Figure 12A:
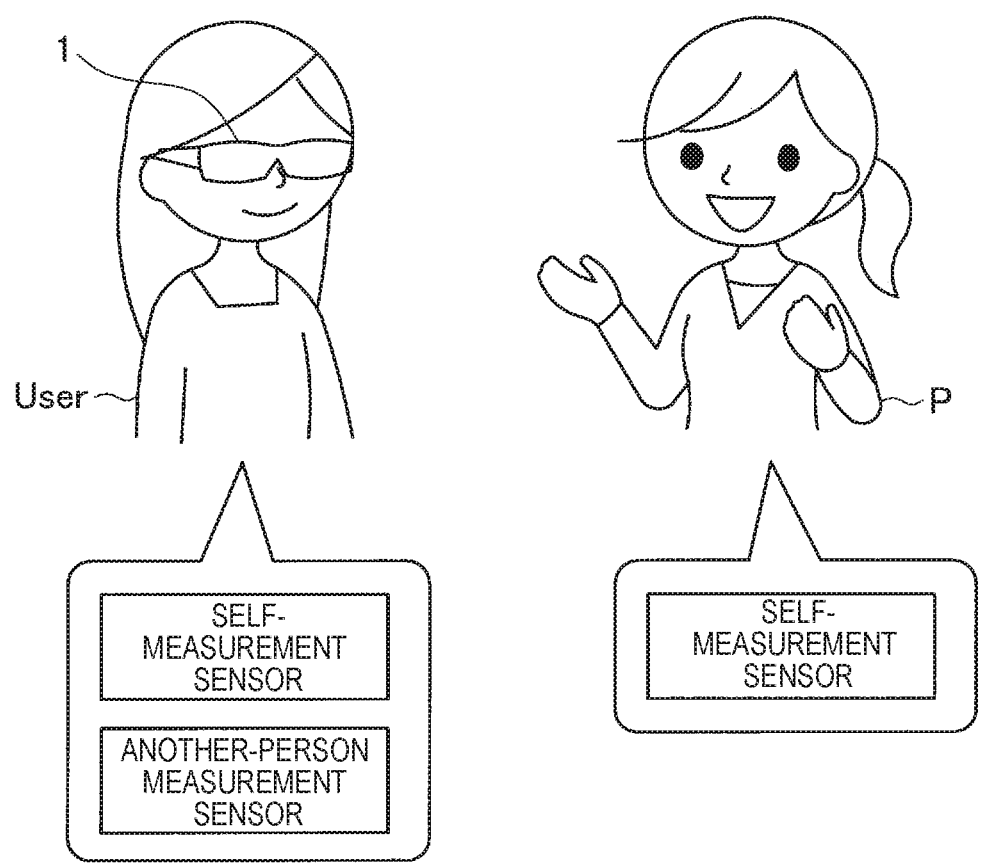
FIG. 12A is a diagram illustrating a case where a self-measurement sensor is also arranged on another-person side.

Subsequently, an information processing system according to a second embodiment of the present disclosure will be described with reference to FIGS. 12A, 12B and FIG. 13. In the above-described first embodiment, the self-measurement sensor is present on the user side as shown in FIG. 1, whilst the present disclosure is not limited to this, but the self-measurement sensor may be present at a person other than the user. For example, in a case where the other person P who is a subject of emotion recognition has agreed to wear a self-measurement sensor, the self-measurement sensor is also arranged on the other person P side as shown in FIG. 12A, and the information processing device 1 can recognize an emotion of the other person P using self-measurement sensor values acquired from two types of self-measurement sensors and an another-person measurement sensor value acquired from the another-person measurement sensor on the user side. In this case, it can be expected that another-person emotion recognition is improved in accuracy.

Figure 12B:
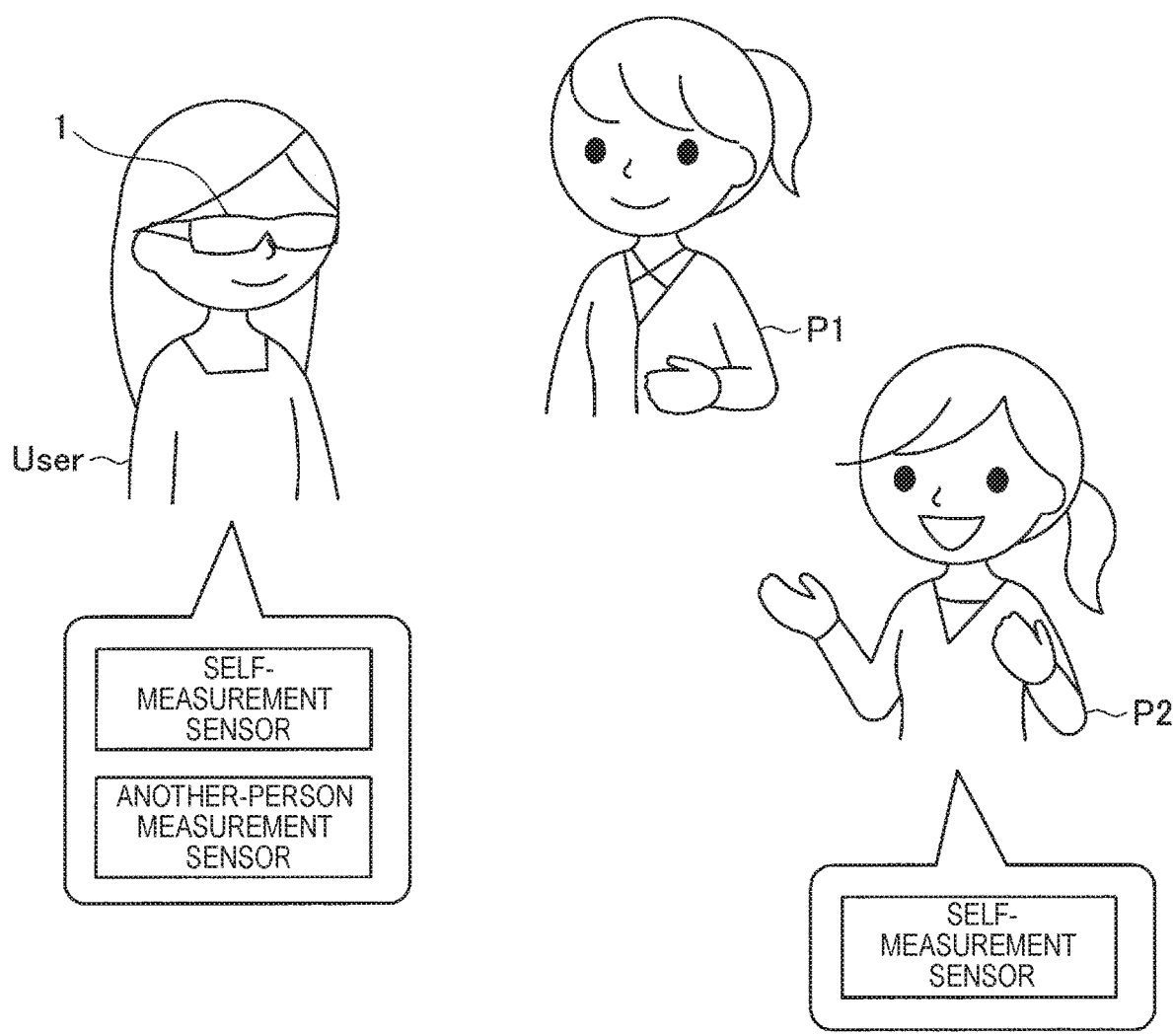
FIG. 12B is a diagram illustrating a case where a self-measurement sensor is also arranged on third party side.

Moreover, in a case where a third party P2 other than the user and the other person P1 has agreed to wear a self-measurement sensor as in FIG. 12B, the self-measurement sensor is also arranged on the third party P2 side, and the information processing device 1 can recognize an emotion of the other person P using self-measurement sensor values acquired from two types of self-measurement sensors and an another-person measurement sensor value acquired from the another-person measurement sensor on the user side. From such a viewpoint that an emotion of the other person P1 also influences an emotion of the third party P2, it can be expected that another-person emotion recognition is also improved in accuracy in this case.

A configuration of an information processing device 1-2 according to the present embodiment in the case of using two types of self-measurement sensors as described above will be described with reference to FIG. 13.

FIG. 13 is a block diagram showing an example of the configuration of the information processing device 1-2 according to the second embodiment. As shown in FIG. 13, the information processing device 1-2 has a first self-measurement-sensor value acquisition unit 10a, a second self-measurement-sensor value acquisition unit 10b, the another-person-measurement-sensor value acquisition unit 11, the another-person emotion recognition unit 12, the emotion recognition management unit 13, the another-person emotion information storage unit 14, the another-person information acquisition unit 15, the another-person information management unit 16, the another-person information storage unit 17, the another-person emotion estimation unit 18, and the output control unit 19.

The configuration of the information processing device 1-2 is different from the configuration of the information processing device 1-1 described with reference to FIG. 2 in that the first self-measurement-sensor value acquisition unit 10a and the second self-measurement-sensor value acquisition unit 10b are included. The first self-measurement-sensor value acquisition unit 10a acquires a sensor value from a self-measurement sensor that senses the user, and outputs the sensor value to the another-person emotion recognition unit 12. Moreover, the second self-measurement-sensor value acquisition unit 10b acquires a sensor value from a self-measurement sensor that senses the other person (partner) or third party, and outputs the sensor value to the another-person emotion recognition unit 12. The self-measurement sensor that senses the other person or third party is worn/held by the other person or third party, and senses biological information and amount-of-activity information of the other person or third party.

Then, the another-person emotion recognition unit 12 recognizes an another-person emotion using the sensor value sensed from the user, the sensor value sensed from the other person or third party, and the sensor value of the other person sensed by the another-person measurement sensor worn/held by the user. In the present embodiment, by using the sensor value sensed from the other person or third party in this manner, another-person emotion recognition is improved in accuracy.

Note that the other components of the information processing device 1-2 are similar to the components having the same names of the information processing device 1-1 described with reference to FIG. 2, and therefore, description is omitted here.

The information processing system according to the second embodiment in the case where the self-measurement sensor is also worn/held on the other person or third party side has been described above.

2-3. Third Embodiment

Next, an information processing system according to a third embodiment of the present disclosure will be described. In the above-described first embodiment, recognition of an another-person emotion is performed on the basis of a sensor value sensed by the self-measurement sensor and a sensor value sensed by the another-person measurement sensor, whilst the present disclosure is not limited to this. For example, in the information processing system according to the present disclosure, it is possible to recognize an another-person emotion without using a sensor value sensed by the another-person measurement sensor. A configuration of such an information processing device 1-3 according to the third embodiment will be specifically described below with reference to FIG. 14.

Figure 14:
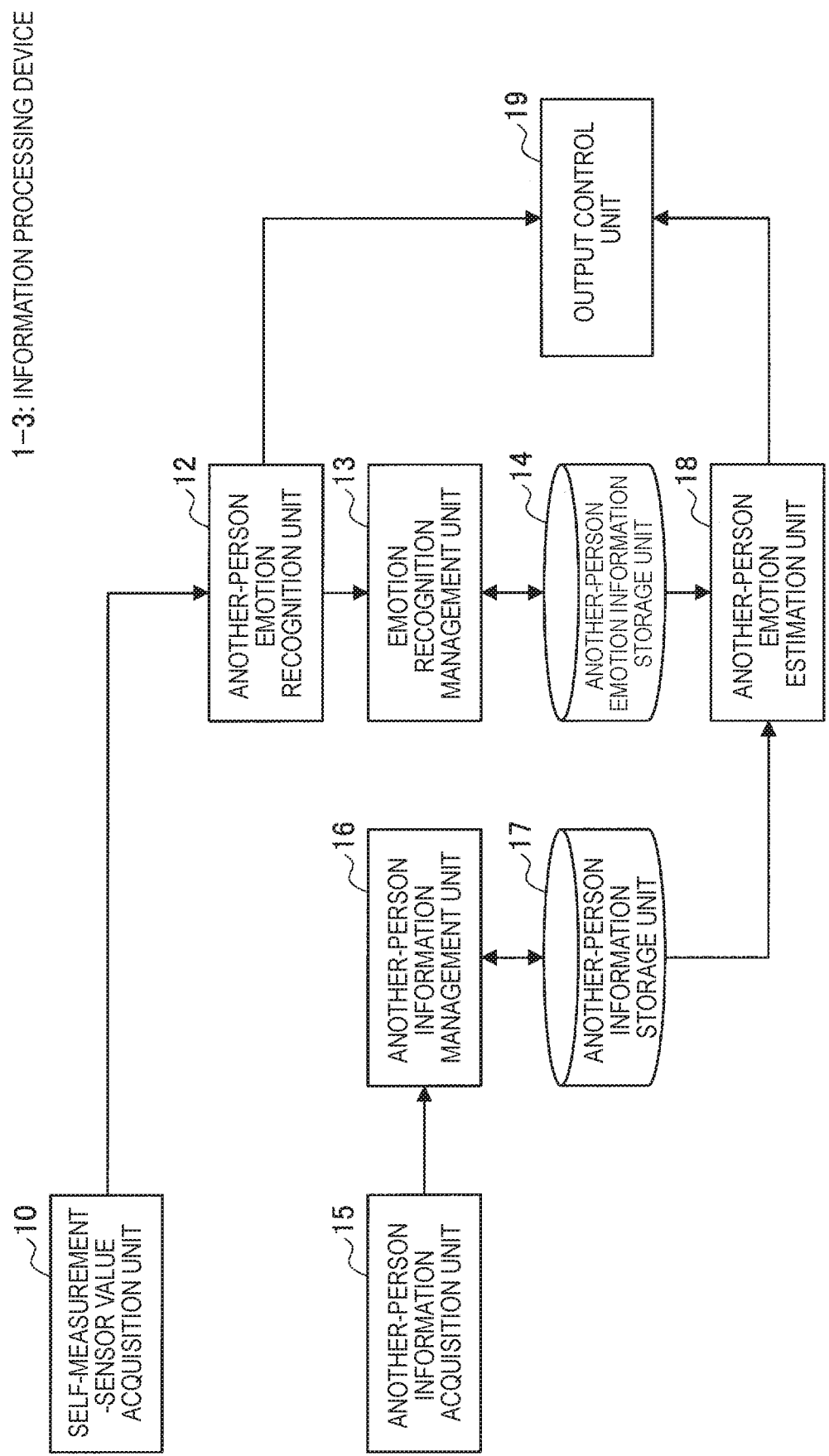
FIG. 14 is a block diagram showing an example of a configuration of an information processing device according to a third embodiment.

FIG. 14 is a block diagram showing an example of a configuration of the information processing device 1-3 according to the third embodiment. As shown in FIG. 14, the information processing device 1-3 has the self-measurement-sensor value acquisition unit 10, the another-person emotion recognition unit 12, the emotion recognition management unit 13, the another-person emotion information storage unit 14, the another-person information acquisition unit 15, the another-person information management unit 16, the another-person information storage unit 17, the another-person emotion estimation unit 18, and the output control unit 19.

As compared with the configuration of the information processing device 1-1 described with reference to FIG. 2, the information processing device 1-3 is different in that the another-person-measurement-sensor value acquisition unit 11 is not included. The another-person emotion recognition unit 12 of the information processing device 1-3 recognizes an another-person emotion only on the basis of a sensor value output from the self-measurement-sensor value acquisition unit 10 (that is, a sensor value sensed from a user by the self-measurement sensor).

Note that the other components of the information processing device 1-3 are similar to the components having the same names of the information processing device 1-1 described with reference to FIG. 2, and therefore, description is omitted here.

In this manner, the information processing device 1-3 according to the third embodiment recognizes an another-person emotion without using the another-person measurement sensor value, which eliminates the need for cost and space for mounting the another-person measurement sensor and can contribute to cost reduction and space reduction of the system.

2-4. Fourth Embodiment

Subsequently, an information processing system according to a fourth embodiment of the present disclosure will be described with reference to FIG. 15 and FIG. 16. It has been described in each of the above-described embodiments that a user is notified of a recognized/estimated another-person emotion by the output control unit 19, whilst the present disclosure is not limited to this, but an action in accordance with the recognized/estimated another-person emotion may be proposed to the user, for example. A configuration of such an information processing device 1-4 according to the fourth embodiment will be described below with reference to FIG. 15.

Figure 15:
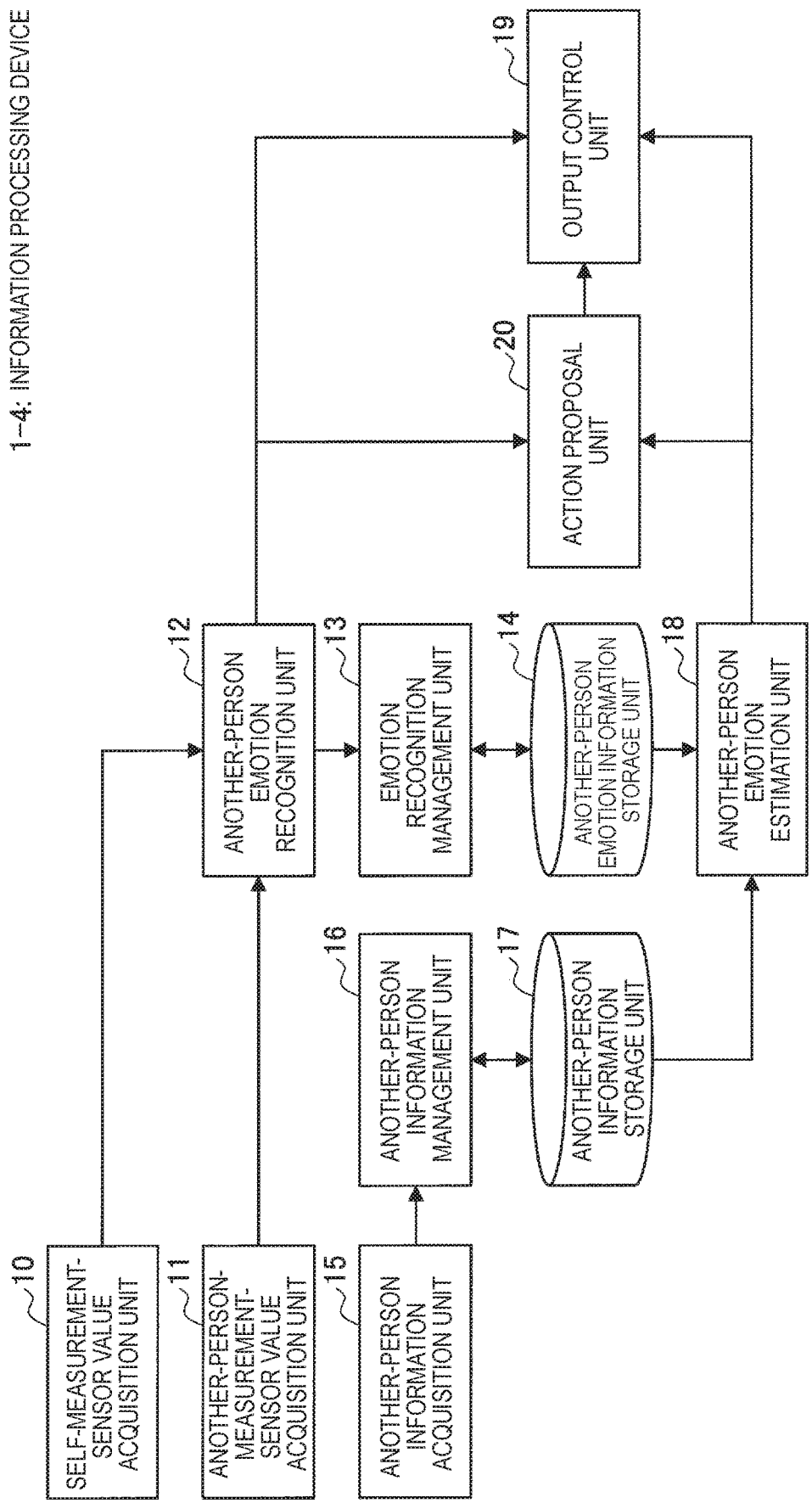
FIG. 15 is a block diagram showing an example of a configuration of an information processing device according to a fourth embodiment.
Figure 16:
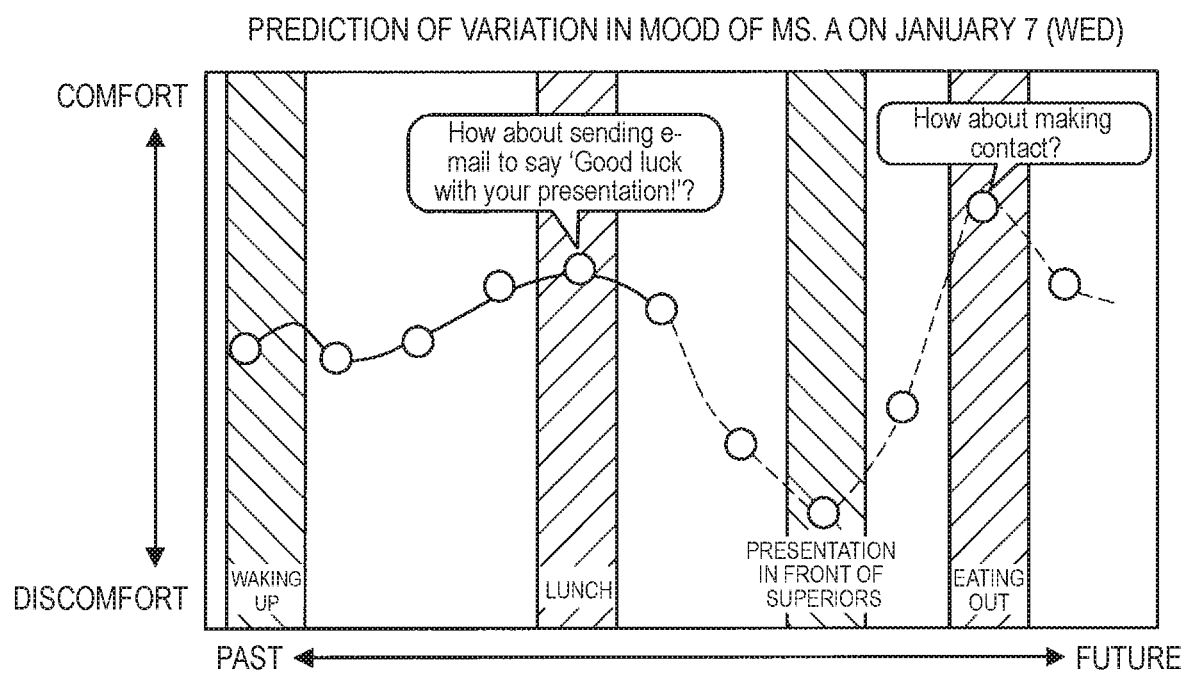
FIG. 16 is a diagram showing an example of action proposals according to the fourth embodiment.

FIG. 15 is a block diagram showing an example of a configuration of the information processing device 1-4 according to the fourth embodiment. As shown in FIG. 15, the information processing device 1-4 has the self-measurement-sensor value acquisition unit 10, the another-person-measurement-sensor value acquisition unit 11, the another-person emotion recognition unit 12, the emotion recognition management unit 13, the another-person emotion information storage unit 14, the another-person information acquisition unit 15, the another-person information management unit 16, the another-person information storage unit 17, the another-person emotion estimation unit 18, the output control unit 19, and an action proposal unit 20.

The action proposal unit 20 proposes an appropriate action to the user on the basis of a current another-person emotion recognized by the another-person emotion recognition unit 12 or an another-person emotion estimated by the another-person emotion estimation unit 18 and another-person information (such as schedule information, ToDo list, positional information, hobby, or preference of the other person). The action proposal unit 20 sends text information or the like that indicates a proposed action to the output control unit 19, and the output control unit 19 explicitly indicates an action proposed to the user together with a notification of an another-person emotion.

Here, an example of an action proposed by the action proposal unit 20 will be described with reference to FIG. 16. FIG. 16 is a diagram showing an example of action proposal according to the fourth embodiment. As shown in FIG. 16, a new action may be proposed to the user together with a graph showing a transition of another-person emotions, for example. More specifically, it is estimated that the mood of another person will be worsened (emotion: tensed, depressed) from the present time (that is, lunchtime) toward an event of "presentation in front of superiors" to be conducted in the afternoon, for example, as shown in FIG. 16, and therefore, an appropriate communication that encourages a partner, such as "How about sending e-mail to say 'Good luck with your presentation!'?" is proposed. It is also estimated that the mood when "eating out" after the event of "presentation in front of superiors" will become good (emotion: delighted, become cheerful), and therefore, an appropriate communication timing for seeing how the partner is, such as "How about making contact?", is proposed.

Furthermore, the action proposal unit 20 is not limited to a proposal of a new action as described above, but may make a proposal to the user with respect to an existing plan in accordance with a recognized/estimated another-person emotion, for example. Specifically, the action proposal unit 20 may propose to the user that "Mr. EEE, the section chief seems to be in a bad mood, so let's postpone the conference about a topic Q scheduled for 10:00 today to 17:00 when Mr. EEE, the section chief will be in a good mood" for postponing an existing plan. The action proposal unit 20 may also propose to the user that "Ms. JJ seems to be in a bad mood, so let's cancel the date with Ms. JJ on Saturday" for suspending an existing plan.

Further, the action proposal unit 20 may propose a new plan to the user in accordance with a recognized/estimated another-person emotion. For example, the action proposal unit 20 proposes such a communication that "Ms. KK seems to be in a good mood after the classes today, so how about asking her to go out?" on the basis of a result of estimating an emotion of a user's friend. Alternatively, the action proposal unit 20 may propose such a task that "Ms. MM will be in a good mood tomorrow morning, so how about performing a task of cleaning a room Z scheduled to do with Ms. MM tomorrow morning?" on the basis of the contents of a ToDo list and a result of estimating another-person emotions.

2-5. Fifth Embodiment

Next, an information processing system according to a fifth embodiment according to the present disclosure will be described. It has been described in each of the above-described embodiments that it is possible to estimate a future another-person emotion by the another-person emotion estimation unit 18 on the basis of another-person information and the another-person emotion history, whilst in the present embodiment, a user is notified of an emotion of another person present at a remote place utilizing the estimation of an another-person emotion. That is, since a future emotion of the other person can be estimated, it is possible to estimate a current emotion of the other person even in a case where the user is not accompanied by the other person, and to notify the user. A configuration of such an information processing device 1-5 according to the fifth embodiment will be specifically described below with reference to FIG. 17.

Figure 17:
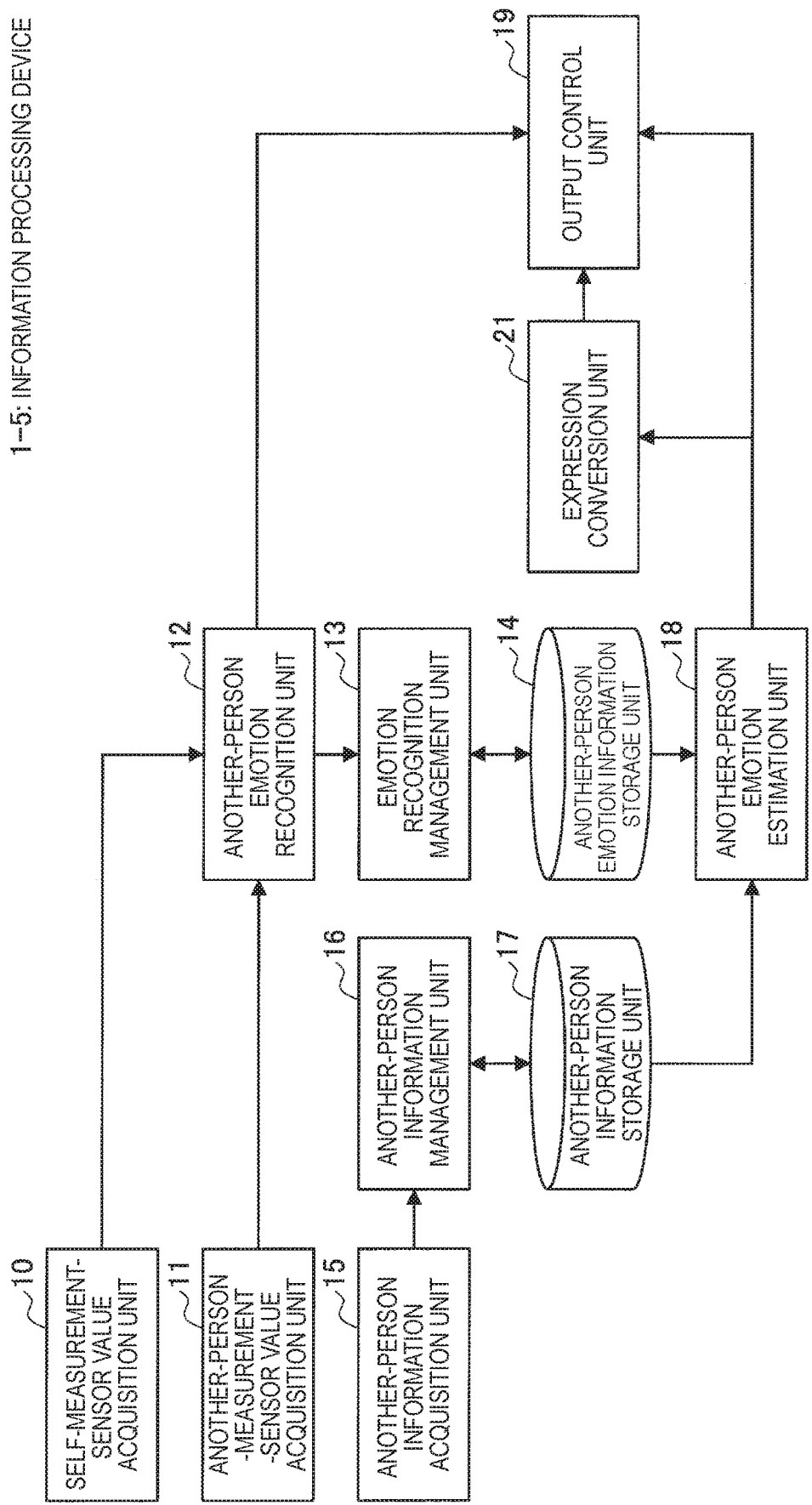
FIG. 17 is a block diagram showing an example of a configuration of an information processing device according to a fifth embodiment.

FIG. 17 is a block diagram showing an example of a configuration of the information processing device 1-5 according to the fifth embodiment. As shown in FIG. 17, the information processing device 1-5 has the self-measurement-sensor value acquisition unit 10, the another-person emotion recognition unit 12, the emotion recognition management unit 13, the another-person emotion information storage unit 14, the another-person information acquisition unit 15, the another-person information management unit 16, the another-person information storage unit 17, the another-person emotion estimation unit 18, the output control unit 19, and an expression conversion unit 21.

The expression conversion unit 21 converts a current emotion of the other person estimated by the another-person emotion estimation unit 18 into an expression. Conversion into an expression is achieved by editing an expression in a face image corresponding to the other person (such as, for example, an avatar, illustration, or actual face image of the other person), for example.

The output control unit 19 notifies the user of a recognized/estimated emotion of the other person, similarly to each of the above-described embodiments. Moreover, the output control unit 19 according to the present embodiment is also capable of explicitly indicating an emotion of the other person as a message originator or destination by the expression converted by the expression conversion unit 21 on an instant message screen that displays an instant message from the other person for notification to the user. Such an instant message screen will be described below with reference to FIG. 18.

Figure 18:
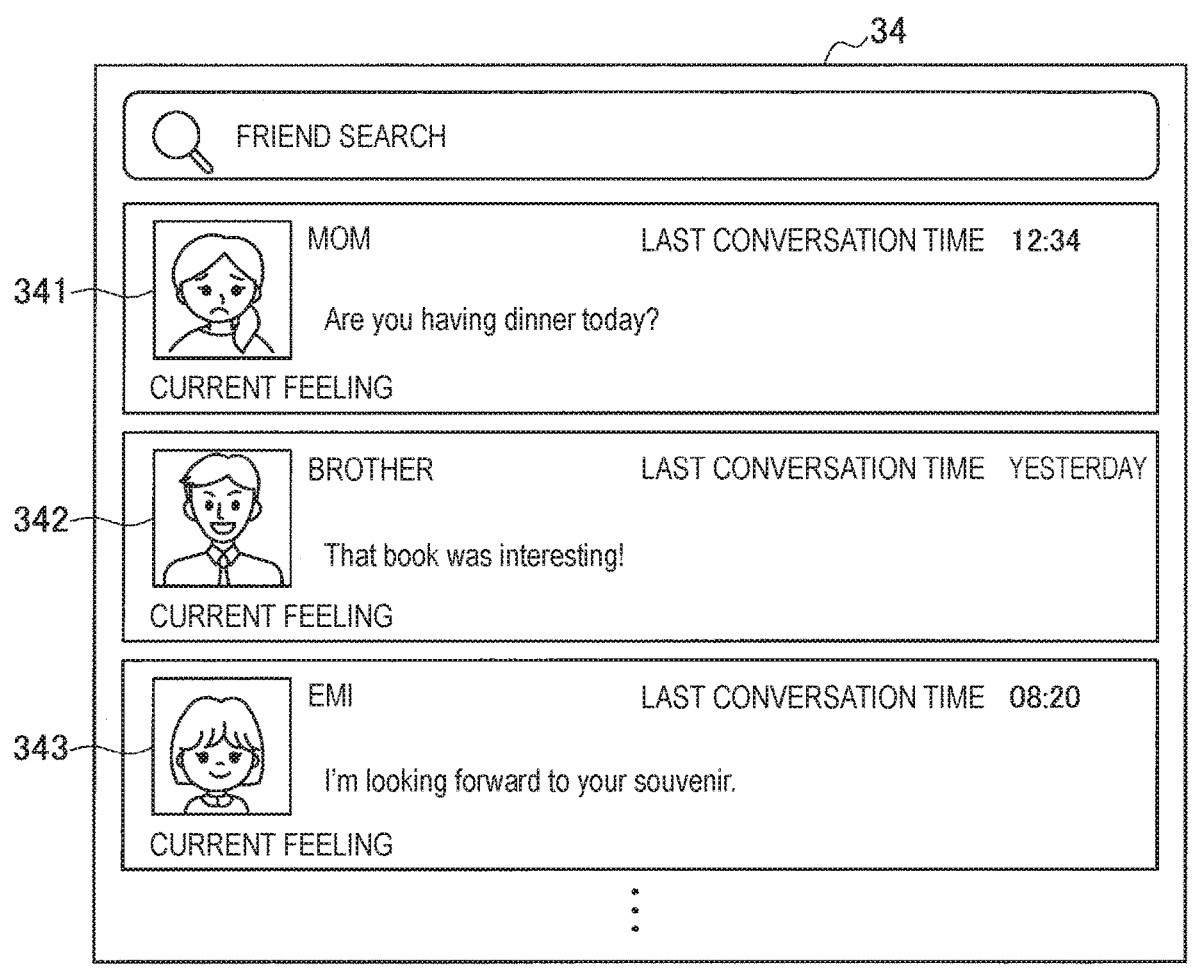
FIG. 18 is a diagram for illustrating an example of an instant message screen according to the fifth embodiment.

FIG. 18 is a diagram for illustrating an example of the instant message screen according to the fifth embodiment. On an instant message screen 34 shown in FIG. 18, the last messages with the respective partners are listed. When one of these partners is selected by the user, the instant message screen 34 transitions to a screen of a message history with the selected partner.

Moreover, on the instant message screen 34, each partner's name, face image, and time of transmission/reception of the last message (that is, the last conversation time) are displayed together with the last message with each partner. Here, face images 341 to 343 of the respective partners displayed on the instant message screen 34 are each converted in real time into an expression in accordance with a current emotion of each partner. A current emotion of each partner may be estimated by the another-person emotion estimation unit 18 using the another-person emotion history and another-person information. That is, in a case where the other person is present at a remote place and is not conducting a conversation with the user, it is not easy to recognize an another-person emotion by the another-person emotion recognition unit 12 using a self-measurement sensor value such as biological information of the user influenced by the another-person emotion as described above, but estimation by the another-person emotion estimation unit 18 on the basis of a past another-person emotion history is possible.

Accordingly, when replying to the last message with "mom" that "Are you having dinner today?", for example, a current emotion of "mom" is reflected on the face image 341, and the user can become aware of the current mood of the partner. In the example shown in FIG. 18, it is estimated that the current mood of "mom" is bad (emotion: sad, depressed), and therefore, the user can delay the timing of replying a message, or send a reply message considering that the partner is in a bad mood (such as "Sorry for my late reply. Please make dinner for me", for example).

In this manner, according to the present embodiment, a current emotion of the other person who is not conducting a conversation with the user and is present at a remote place can be estimated and the user can be notified thereof, and the user can send an optimal message upon grasping an emotion of the partner.

Note that an another-person emotion is converted into an expression by the expression conversion unit 21 and the user is notified thereof in the present embodiment, whilst the present embodiment is not limited to this, but an another-person emotion may be converted into text or color, for example, and the user may be notified thereof. For example, on the instant message screen, text such as "good mood" or "bad mood" is shown, or good or bad of the mood is shown in predetermined colors (such as by representing the partner's name or display area in warm colors when the mood is good, and in cold colors when the mood is bad, for example) in correspondence to the partner's name or profile image (such as an icon or face image).

3. Hardware Configuration of the Information Processing Device 1

The information processing devices 1-1 to 1-5 according to the respective embodiments of the present disclosure have been described above. Each function of the above-described information processing devices 1-1 to 1-5 is implemented by cooperation between software and hardware which will be described below.

Figure 19:
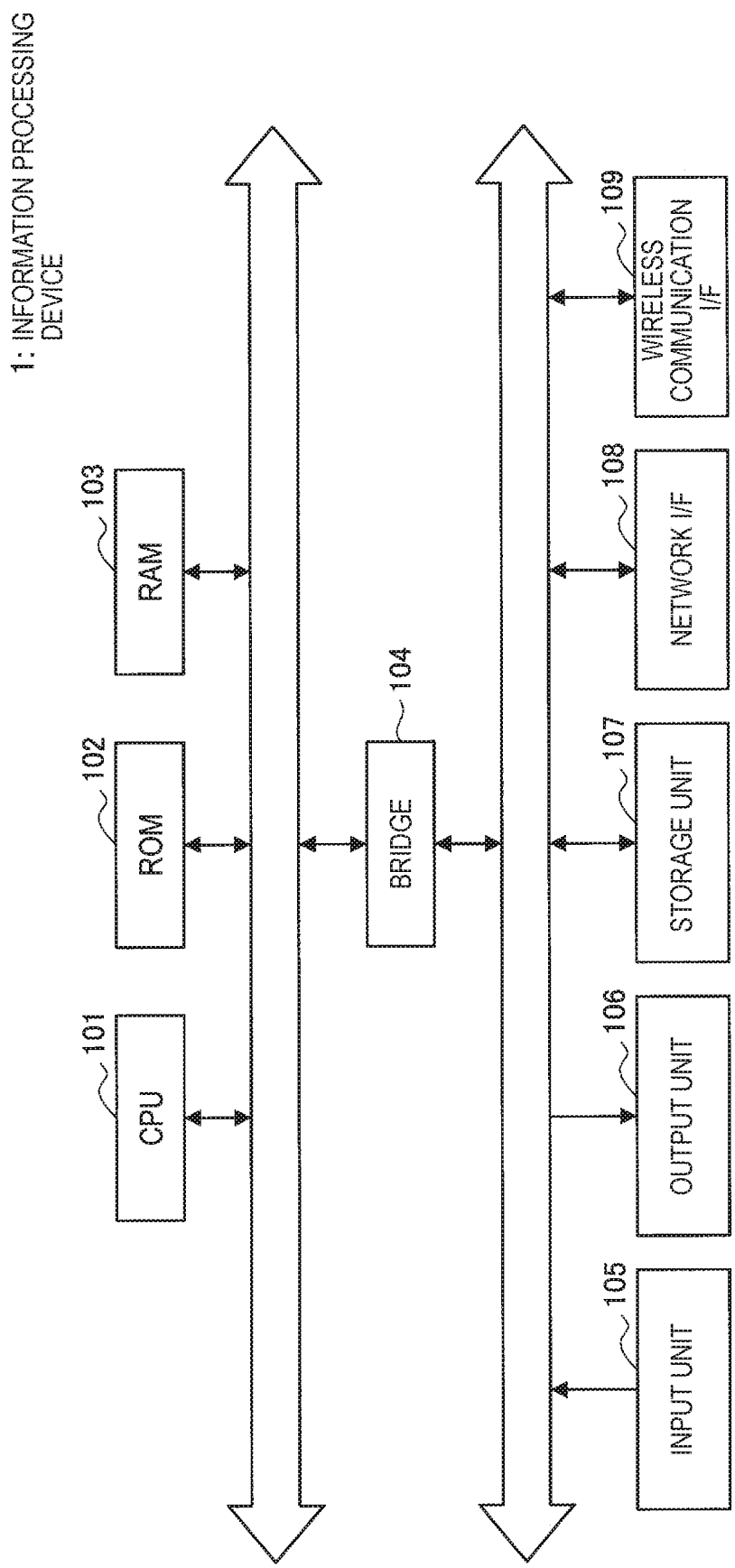
FIG. 19 is an explanatory drawing showing a hardware configuration of an information processing device according to an embodiment of the present disclosure.

FIG. 19 is an explanatory drawing showing a hardware configuration of the information processing device 1 according to an embodiment of the present disclosure. As shown in FIG. 19, the information processing device 1 includes a central processing unit (CPU) 101, a read only memory (ROM) 102, a random access memory (RAM) 103, a bridge 104, an input unit 105, an output unit 106, a storage unit 107, a network interface (I/F) 108, and a wireless communication I/F 109.

The CPU 101 functions as an arithmetic processing device, and cooperates with various programs to implement operations of the self-measurement-sensor value acquisition unit 10, the another-person-measurement-sensor value acquisition unit 11, the another-person emotion recognition unit 12, the emotion recognition management unit 13, the another-person information acquisition unit 15, the another-person information management unit 16, the another-person emotion estimation unit 18, the output control unit 19, the action proposal unit 20, and the expression conversion unit 21 in the information processing device 1. Moreover, the CPU 101 may be a microprocessor. The ROM 102 stores a program, an arithmetic parameter, or the like that the CPU 101 uses. The RAM 103 temporarily stores a program used in execution of the CPU 101, a parameter that changes as necessary in execution, or the like. Part of the another-person emotion information storage unit 14 and the another-person information storage unit 17 in the information processing device 1 is implemented by the ROM 102 and the RAM 103. The CPU 101, the ROM 102, and the RAM 103 are connected to one another with an internal bus configured with a CPU bus or the like.

The input unit 105 is configured with input means for a user to input information, such as a mouse, keyboard, touch panel, button, microphone, camera, switch, and lever, an input control circuit that generates an input signal on the basis of an input made by the user and outputs the input signal to the CPU 101, and the like. The user of the information processing device 1 can input various types of data or instruct a processing operation to the information processing device 1 by operating the input unit 105.

The output unit 106 performs an output to a display device, such as a lens unit (an example of a transparent display unit) that provides display using a hologram optical technology, for example, a liquid crystal display (LCD) device, or an organic light emitting diode (OLED) device. Furthermore, the output unit 106 may perform an audio output through a speaker or headphone.

The storage unit 107 is a device for storing data. The storage unit 107 may include a storage medium, a recording device that records data in the storage medium, a readout device that reads out data from the storage medium and a deletion device that deletes data recorded in the storage medium, or the like. The storage unit 107 stores programs and various types of data that the CPU 101 executes.

The network I/F 108 is a communication interface configured with a communication device for connection to a network. Moreover, the network I/F 108 may be a communication apparatus adaptable to wireless local area network (LAN) or a communication apparatus adaptable to long term evolution (LTE). The network I/F 108 constitutes a part of the another-person information acquisition unit 15, and the another-person information acquisition unit 15 is capable of acquiring another-person information from a predetermined server on a network.

The wireless communication I/F 109 is a communication interface for connection to an information processing device or peripheral equipment external to the information processing device 1. Note that it is configured to include the wireless communication I/F 109 here as an example, whilst a communication interface that connects to an external information processing device or peripheral equipment by wired communication may be adopted.

4. Conclusion

As described above, in the information processing systems according to the embodiments of the present disclosure, it is possible to recognize an emotion of another user (another person) using sensing information of the user. Accordingly, the other person is not forced to wear a sensor device when recognizing an emotion of the other person, and a more practical system can be implemented, which improves convenience.

Moreover, in the information processing systems according to the present embodiments, by notifying the user of an emotion of another person in real time while the user is conducting a conversation or the like with the other person, the user can take measures in consideration of the partner's mood. In addition, in the information processing systems according to the present embodiments, by estimating a future another-person emotion and notifying the user in advance, the user can change a plan or take an action in consideration of the partner's mood.

In addition, in the information processing systems according to the present embodiments, it is also possible to make an appropriate action proposal to the user in accordance with an another-person emotion as well as notifying the user of a current emotion of the other person and a future emotion of the other person.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, it is also possible to create a computer program for causing hardware, such as the CPU 101, the ROM 102, and the RAM 103 built in the above-described information processing device 1, to exert functions of the information processing device 1. Moreover, a computer-readable storage medium having the computer program recorded therein is also provided.

Furthermore, it is not necessarily required to process the respective steps in the operation of the information processing device 1 in the present specification in a time series manner in the order described as a flowchart. For example, the respective steps in the operation of the information processing device 1 may be processed in an order different from the order described as a flowchart, or may be processed in parallel. Specifically, step S103 and step S106 shown in FIG. 6 may be performed in the reverse order or simultaneously, and step S115 and step S118 may be performed in the reverse order or simultaneously.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An information processing device including:

an emotion recognition unit configured to recognize, on the basis of information concerning a user and information concerning another user having been sensed, an emotion of the other user; and a notification control unit configured to perform control such that the user is notified of information concerning the emotion of the other user having been recognized.

(2)

The information processing device according to (1), in which the information concerning the user is biological information of the user.

(3)

The information processing device according to (2), in which the biological information includes a heart rate sensor value or a sweat sensor value, and the emotion recognition unit recognizes the emotion of the other user on the basis of a feature quantity extracted from the biological information.

(4)

The information processing device according to (2) or (3), in which the emotion recognition unit recognizes, as the emotion of the other user, an emotion that matches, resembles, or correlates with an emotion of the user recognized on the basis of a feature quantity extracted from the biological information.

(5)

The information processing device according to any one of (2) to (4), in which the information concerning the user further includes amount-of-activity information of the user.

(6)
The information processing device according to (5), in which
the amount-of-activity information includes an acceleration sensor value, an angular velocity sensor value, a pedometer value, or a geomagnetic sensor value.

(7)
The information processing device according to any one of (2) to (6), in which
information concerning the other user is expression information of the other user.

(8)
The information processing device according to (7), in which
the expression information includes a position of a corner of a mouth or an eyebrow based on a feature point extracted from a face image obtained by imaging the other user, and
the emotion recognition unit recognizes the emotion of the other user further on the basis of a feature quantity extracted from the expression information.

(9)
The information processing device according to (7) or (8), in which
the information concerning the other user includes collected voice information of the other user, sensed posture information, or temperature information acquired from an infrared image.

(10)
The information processing device according to any one of (2) to (9), in which
the information concerning the user and the information concerning the other user are obtained from a sensor device held by the user.

(11)
The information processing device according to any one of (2) to (10), in which
the emotion recognition unit recognizes the emotion of the other user with reference to sensed biological information of a third party.

(12)
The information processing device according to any one of (1) to (11), further including:
an emotion estimation unit configured to estimate a future emotion of the other user on the basis of an another-user emotion history extracted from a storage unit that accumulates the information concerning the emotion of the other user recognized by the emotion recognition unit.

(13)
The information processing device according to any one of (1) to 12, in which
the notification control unit performs control such that a transition of the emotion of the other user is displayed in a time series manner.

(14)
The information processing device according to (12), in which
the notification control unit performs control such that an emotion forecast of the other user is displayed on the basis of a result of estimation by the emotion estimation unit.

(15)
The information processing device according to any one of (1) to (14), further including:
an action proposal unit configured to propose a predetermined action to the user in accordance with the emotion of the other user.

(16)
The information processing device according to (12), in which
the emotion estimation unit estimates a current emotion of the other user, and
the notification control unit performs control such that the user is notified in real time of the emotion of the other user having been estimated.

(17)
The information processing device according to (12) or (16), in which
the emotion estimation unit estimates the emotion of the other user on the basis of the another-user emotion history and action-related information of the other user.

(18)
A control method including:
recognizing, on the basis of information concerning a user and information concerning another user having been sensed, an emotion of the other user; and
performing control by a notification control unit such that the user is notified of information concerning the emotion of the other user having been recognized.

(19)
A program for causing a computer to function as:
an emotion recognition unit configured to recognize, on the basis of information concerning a user and information concerning another user having been sensed, an emotion of the other user; and
a notification control unit configured to perform control such that the user is notified of information concerning the emotion of the other user having been recognized.

REFERENCE SIGNS LIST 1, 1-1 to 1-5 information processing device
10 self-measurement sensor value acquisition unit
10a first self-measurement sensor value acquisition unit
10b second self-measurement sensor value acquisition unit
11 another-person measurement sensor value acquisition unit
12 another-person emotion recognition unit
13 emotion recognition management unit
14 another-person emotion information storage unit
15 another-person information acquisition unit
16 another-person information management unit
17 another-person information storage unit
18 another-person emotion estimation unit
19 output control unit
20 action proposal unit
21 expression conversion unit
P, P1 another person
P2 third party

The invention claimed is:
1. An information processing device, comprising:
a central processing unit (CPU) configured to:
acquire a first sensor value from a first measurement sensor and a second sensor value from a second measurement sensor, wherein
each of the first measurement sensor and the second measurement sensor is one of wearable or holdable by a first user,
the first sensor value corresponds to biological information of the first user,
the second sensor value corresponds to expression information of a second user, and
the second user is an interaction partner of the first user;

recognize, based on the biological information of the first user and the expression information of the second user, a first emotion of the second user, wherein the first emotion of the second user corresponds to an emotion of the second user at a current time;
propose a specific action to the first user based on the first emotion of the second user and user information of the second user, wherein the user information of the second user includes at least one of schedule information, positional information, or preference information of the second user;
estimate a future emotion of the second user based on an emotion history of the second user, wherein the future emotion of the second user corresponds to an emotion of the second user at a time in future;
compare the future emotion of the second user with the first emotion of the second user;
determine a change in a mood of the second user based on the comparison of the future emotion of the second user with the first emotion of the second user; and
control, based on the first emotion of the second user, concurrent display of a notification and information indicating the proposed specific action to the first user, wherein the notification to the first user includes a result of the determination of the change in the mood of the second user.

2. The information processing device according to claim 1, wherein
the biological information of the first user includes one of a heart rate sensor value or a sweat sensor value, and
the CPU is further configured to:
extract a feature quantity from the biological information of the first user; and
recognize the first emotion of the second user based on the feature quantity extracted from the biological information of the first user.

3. The information processing device according to claim 1, wherein the CPU is further configured to:
extract a feature quantity from the biological information of the first user;
recognize an emotion of the first user based on the feature quantity extracted from the biological information of the first user; and
recognize, as the first emotion of the second user, a second emotion that one of matches, resembles, or correlates with the emotion of the first user.

4. The information processing device according to claim 1, wherein the first sensor value further corresponds to amount-of-activity information of the first user.

5. The information processing device according to claim 4, wherein the amount-of-activity information includes one of an acceleration sensor value, an angular velocity sensor value, a pedometer value, or a geomagnetic sensor value.

6. The information processing device according to claim 1, wherein
the expression information includes a position of a corner of one of a mouth or an eyebrow of the second user based on a feature point extracted from a face image of the second user, and
the CPU is further configured to:
extract a feature quantity from the expression information; and
recognize the first emotion of the second user based on the feature quantity extracted from the expression information.

7. The information processing device according to claim 1, wherein the second sensor value further corresponds to one of collected voice information of the second user, sensed posture information of the second user, or temperature information of the second user acquired from an infrared image.

8. The information processing device according to claim 1, wherein the CPU is further configured to recognize the first emotion of the second user based on biological information of a third party.

9. The information processing device according to claim 1, wherein the CPU is further configured to:
accumulate information regarding the first emotion of the second user in a database; and
extract the emotion history of the second user from the database.

10. The information processing device according to claim 9, wherein
the CPU is further configured to control display of an emotion forecast of the second user, and
the display of the emotion forecast is based on a result of the estimation of the future emotion of the second user.

11. The information processing device according to claim 9, wherein the CPU is further configured to:
recognize the first emotion of the second user based on action-related information of the second user and the emotion history of the second user; and
control, based on the recognized first emotion of the second user, display of the notification to the first user.

12. The information processing device according to claim 9, wherein the CPU is further configured to estimate the future emotion of the second user based on the emotion history of the second user and action-related information of the second user.

13. The information processing device according to claim 1, wherein the notification includes a graphical representation of a transition of the first emotion of the second user in a time series manner.

14. A control method, comprising:
in an information processing device that includes a central processing unit (CPU):
acquiring, by the CPU, a first sensor value from a first measurement sensor and a second sensor value from a second measurement sensor, wherein
each of the first measurement sensor and the second measurement sensor is one of wearable or holdable by a first user,
the first sensor value corresponds to biological information of the first user,
the second sensor value corresponds to expression information of a second user, and
the second user is an interaction partner of the first user;
recognizing, by the CPU, a current emotion of the second user based on the biological information of the first user and the expression information of the second user, wherein the current emotion of the second user corresponds to an emotion of the second user at a current time;
proposing, by the CPU, a specific action to the first user based on the current emotion of the second user and user information of the second user, wherein the user information of the second user includes at least one of schedule information, positional information, or preference information of the second user;
estimating, by the CPU, a future emotion of the second user based on an emotion history of the second user, wherein the future emotion of the second user corresponds to an emotion of the second user at a time in future;

comparing, by the CPU, the future emotion of the second user with the current emotion of the second user;

determining, by the CPU, a change in a mood of the second user based on the comparison of the future emotion of the second user with the current emotion of the second user; and controlling, by the CPU based on the emotion of the second user, concurrent display of a notification and information indicating the proposed specific action to the first user, wherein the notification to the first user includes a result of the determination of the change in the mood of the second user.

15. A non-transitory computer-readable medium having stored thereon computer-executable instructions which, when executed by a processor, cause the processor to execute operations, the operations comprising:

acquiring a first sensor value from a first measurement sensor and a second sensor value from a second measurement sensor, wherein each of the first measurement sensor and the second measurement sensor is one of wearable or holdable by a first user, the first sensor value corresponds to biological information of the first user, the second sensor value corresponds to expression information of a second user, and the second user is an interaction partner of the first user;

recognizing, based on the biological information of the first user and the expression information of the second user, a current emotion of the second user, wherein the current emotion of the second user corresponds to an emotion of the second user at a current time;

proposing a specific action to the first user based on the current emotion of the second user and user information of the second user, wherein the user information of the second user includes at least one of schedule information, positional information, or preference information of the second user;

estimating a future emotion of the second user based on an emotion history of the second user, wherein the future emotion of the second user corresponds to an emotion of the second user at a time in future;

comparing the future emotion of the second user with the current emotion of the second user;

determining a change in a mood of the second user based on the comparison of the future emotion of the second user with the current emotion of the second user; and controlling, based on the emotion of the second user, concurrent display of a notification and information indicating the proposed specific action to the first user, wherein the notification to the first user includes a result of the determination of the change in the mood of the second user.

* * * * *